United States Patent
Pietri et al.

(10) Patent No.: US 6,528,656 B1
(45) Date of Patent: Mar. 4, 2003

(54) LINEAR OR CYCLIC AMINOPHOSPHONATES AS PH MARKERS IN PHOSPHORUS 31 NMR SPECTROSCOPY

(75) Inventors: Sylvia Pietri, Martigues (FR); François Le Moigne, Marseilles (FR); Malvina Miollan, Dabisse (FR); Marcel Culcasi, Martigues (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 09/646,430

(22) PCT Filed: Mar. 18, 1999

(86) PCT No.: PCT/FR99/00631
§ 371 (c)(1),
(2), (4) Date: Nov. 16, 2000

(87) PCT Pub. No.: WO99/47527
PCT Pub. Date: Sep. 23, 1999

(30) Foreign Application Priority Data

Mar. 18, 1998 (FR) ............................................. 98 03317

(51) Int. Cl.⁷ .......................... C07F 9/40; C07F 9/572; G01N 31/22
(52) U.S. Cl. ...................... 548/412; 558/166; 436/163
(58) Field of Search .................... 558/166; 548/412; 436/163

(56) References Cited

U.S. PATENT DOCUMENTS

| | | | |
|---|---|---|---|
| 2,635,112 A | 4/1953 | Fields | ......................... 558/166 |
| 3,907,652 A | 9/1975 | Wagenknecht et al. | ...... 558/166 |
| 4,005,160 A | 1/1977 | Redmore et al. | ............ 558/166 |

FOREIGN PATENT DOCUMENTS

| | | | |
|---|---|---|---|
| DE | 41 00 856 | | 10/1991 |
| EP | 0 153 284 | | 8/1985 |
| EP | 0 184 753 | | 6/1986 |
| FR | 2 639 350 | | 5/1990 |
| FR | 2 707 990 | | 1/1995 |
| GB | 1015616 | * | 1/1966 |
| GB | 1354343 | * | 5/1974 |
| PL | 0112289 | * | 2/1982 |
| PL | 0148859 | * | 5/1990 |
| WO | WO 95/25111 | | 9/1995 |

OTHER PUBLICATIONS

Aksinenko et al, Chemical Abstracts, vol. 108, # 186848j (1988).*
Belov et al, Chemical Abstracts, vol. 87, # 135669s (1977).*
Lakota et al, Chemical Abstracts, vol. 120, # 292019x (1994).*
Rockenbauer et al, Chemical Abstracts, vol. 127, #278235c (1997).*
Roubaud et al II, Chemical Abstracts, vol. 125, #168147b (1996).*
Rockenbauer et al., "Combined Ring Inversion and Side Group Rotation in Geminal Diphosphoryl Substituted Pyrrolidinoxyl Radicals: ESR Analysis of Chemical Exchange between Four Nonequivalent Sites", *Chemical Abstracts*, vol. 127, No. 20, 278235c, Nov. 1997.
V. Roubaud et al., "Conformational analysis of dialykyl (2,5–dialkyl pyrrolidin–2–yl) phosphonate by x–ray analysis, NMR and force field calculations", *Chemical Abstracts*, vol. 125, No. 13, 168147b, Sep. 1996.
F. Brenot et al., "Kinetics of endosomal acidification in *Dictyostelium discoideum* amoebae. $^{31}$P–NMR evidence for a very acidic early endosomal compartment", *Biochimie*, 1992, vol. 74, pp. 883–895.
P.M.L. Robitaille et al., "An Analysis of the pH–Dependent Chemical–Shift Behavior of Phosphorus–Containing Metabolites", *Journal of Magnetic Resonance*, vol. 92, 1991, pp. 73–84.
H. Sasai et al., "Catalytic Asymmetric Synthesis of α–Amino Phosphonates Using Lanthanoid–Potassium–BINOL Complexes", *The Journal of Organic Chemistry*, vol. 60, No. 21, Oct. 1995, pp. 6656–6657.
R.J. Gillies et al., "$^{31}$–P–MRS measurements of extracellular pH of tumors using 3–aminopropylphosphonate", *Am. J. Physiol.*, vol. 267, 1994, pp. C195–C203.
M. DeFronzo et al., "Characterization of Methylphosphonate as a $^{31}$P NMR pH Indicator", *The Journal of Biological Chemistry*, vol. 262, No. 23, Aug. 1987, pp. 11032–11037.

* cited by examiner

Primary Examiner—Fiona T. Powers
(74) Attorney, Agent, or Firm—Young & Thompson

(57) ABSTRACT

Linear or cyclic aminophosphonates are disclosed which are useful as pH markers. A method of using the linear or cyclic aminophosphonates in phosphorus-31 NMR spectroscopy is also disclosed.

28 Claims, 6 Drawing Sheets

Figure 1:
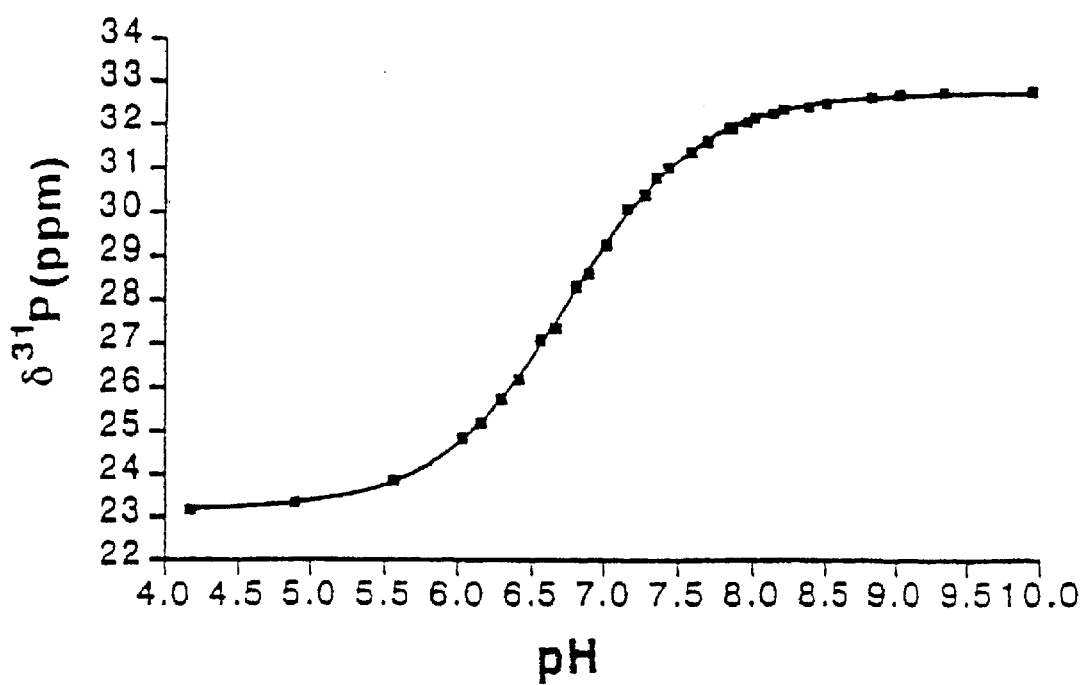

LINEAR OR CYCLIC AMINOPHOSPHONATES AS PH MARKERS IN PHOSPHORUS 31 NMR SPECTROSCOPY

The invention relates to novel linear or cyclic aminophosphonates and to their use as pH markers in phosphorus-31 NMR spectroscopy, More generally, the A invention relates to the use of aminophosphonate derivatives as pH markers in NMR spectroscopy. Phosphorus-31 NMR spectroscopy has been found to be an effective means for measuring extracellular and intracellular pH in vivo.

The advantage of this method is that it does not at all disrupt the medium on which the measurement is taken, which is an essential condition for an in vivo measurement. A compound can be used as a pH marker when the numerical value of the chemical shift of the resonance peak obtained by $^{31}$P NMR varies as a function of the pH of the medium into which the compound has been introduced. The difficulty consists in developing the ideal, non-toxic compound which will be able to function as a pH marker in a broad pH range, with good sensitivity. An additional requirement is that the measurement should be little, if at all, affected by the other constituents of the physiological medium and that it should only react to a pH variation, even a very small one.

A certain number of markers are commonly proposed in the art. The one most commonly used is inorganic phosphate Pi, which has the advantage of being an endogenous compound present in all cells. However, this marker has two major drawbacks which may prevent the production of precise measurements (R. J. Gillies et al. (1986) Proc. Soc. Magn. Reson. Med. 5, 153–154):

the Pi content is generally relatively low in the cell and varies with the metabolic state of the cell;

the lack of sensitivity of this compound does not make it possible to distinguish between extra-cellular and intra-cellular pH.

2-Deoxyglucose 6-phosphate and methyl phosphonate have also been tested (M. DeFronzo et al., (1987) J. Biol. Chem. 262, 11032–11037). The results of these studies show that methyl phosphonate is a much more sensitive marker than 2-deoxyglucose 6-phosphate. Furthermore, although the latter compound is not metabolized, it is found to be toxic to the cell. On the other hand, despite its low toxicity, methyl phosphonate has the major drawback of total permeability with respect to cell membranes in the case of the tumour cell line studied.

Phenyl phosphonate is another extracellular pH marker (cf. Circulation Research, vol. 60, No. 4, 1987, 472–477). The drawback of this compound is that the $^{31}$P chemical shift is influenced by the presence of specific ions in the measuring medium. The American Physiological Society, 1994, C195–C203 moreover reports the possibility of using 3-aminopropyl phosphonate as an extracellular pH indicator.

The present inventors have discovered a family of molecules, namely linear or cyclic aminophosphonates, which are particularly advantageous since they lead to improved sensitivity in measuring pH and since they make it possible to cover a whole range of different pH values depending on the substituents, thus allowing high precision as regards measurement at more acidic or more basic pH values. These molecules are moreover relatively non-toxic.

Only some of these aminophosphonates are novel. These novel compounds have the formula (I.1) or (I.2):

Formula (I.1)

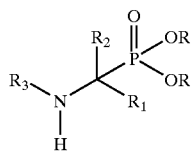

in which:

R represents a $(C_1-C_{18})$alkyl or $(C_6-C_{10})$aryl group;

$R_1$ and $R_2$ independently represent a deuterium atom; a halogen atom; a $(C_1-C_{18})$alkyl group optionally substituted with one or more radicals chosen from $(C_1-C_6)$alkoxy, $(C_3-C_{11})$cycloalkyl, halogen, $(C_6-C_{10})$aryl and nitro; a $(C_6-C_{10})$aryl group optionally substituted with one or more radicals chosen from $(C_1-C_6)$alkyl, $(C_1-C_6)$alkoxy, halogen, nitro and $(C_3-C_{11})$cycloalkyl; $(C_1-C_8)$alkoxy optionally substituted with one or more radicals chosen from $(C_1-C_6)$alkoxy, halogen, nitro, $(C_3-C_{11})$cycloalkyl and $(C_6-C_{10})$aryl; a nitro group; or a $(C_3-C_{11})$cycloalkyl group optionally substituted with one or more radicals chosen from $(C_1-C_6)$alkyl, $(C_1-C_6)$alkoxy, halogen and nitro;

$R_3$ represents a hydrogen or deuterium atom; an n-propyl group or a linear $(C_5-C_{18})$alkyl group, optionally substituted with one or more radicals chosen from: nitro, halogen, $(C_1-C_6)$alkoxy and $(C_3-C_{11})$cycloalkyl; a $(C_3-C_{11})$cycloalkyl group optionally substituted with one or more radicals chosen from $(C_1-C_6)$alkyl, $(C_1-C_6)$alkoxy, halogen and nitro;

and the salts thereof with a pharmaceutically acceptable acid.

Formula (I.2)

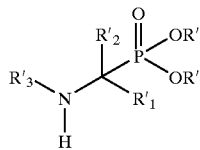

in which

R' represents a hydrogen atom or a $(C_1-C_{18})$alkyl or $(C_6-C_{10})$aryl group;

$R'_1$ represents a hydrogen atom; a deuterium atom; a halogen atom; a $(C_1-C_{18})$alkyl group optionally substituted with one or more radicals chosen from $(C_1-C_6)$alkoxy, $(C_3-C_{11})$cycloalkyl, halogen, $(C_6-C_{10})$aryl and nitro; a $(C_6-C_{10})$aryl group optionally substituted with one or more radicals chosen from $(C_1-C_6)$alkyl, $(C_1-C_6)$alkoxy, halogen, nitro and $(C_3-C_{11})$cycloalkyl; $(C_1-C_{18})$alkoxy optionally substituted with one or more radicals chosen from $(C_1-C_6)$ alkoxy, halogen, nitro, $(C_3-C_{11})$cycloalkyl and $(C_6-C_{10})$ aryl; a nitro group; or a $(C_3-C_{11})$cycloalkyl group optionally substituted with one or more radicals chosen from $(C_1-C_6)$ alkyl, $(C_1-C_6)$alkoxy, halogen and nitro;

$R'_2$ and $R'^3$ together form a divalent radical:

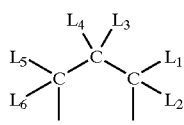
(a)

in which the group —C($L_1$)($L_2$)— is directly linked to the carbon bearing $R'_1$, and in which $L_1$, $L_2$, $L_3$ and $L_4$ represent, independently of each other, a hydrogen atom, a deuterium atom or a ($C_1$–$C_{18}$)alkyl or ($C_6$–$C_{10}$)aryl group;

$L_5$ and $L_6$ being defined as follows:
  when $R'_1$ represents a hydrogen, halogen or deuterium atom, an optionally substituted ($C_1$–$C_{18}$) alkoxy group, a nitro group or an optionally substituted ($C_3$–$C_{11}$)cycloalkyl group, $L_5$ and $L_6$ represent, independently of each other, a hydrogen atom, a deuterium atom, a ($C_1$–$C_{18}$)alkyl group, a ($C_6$–$C_{10}$)aryl group or a group —P(O)(OR')$_2$;
  when $R'_1$ represents an optionally substituted ($C_1$–$C_{18}$)alkyl or optionally substituted ($C_6$–$C_{10}$) aryl, either $L_5$ or $L_6$ represents a hydrogen atom, and the other represents ($C_2$–$C_{18}$)alkyl or ($C_6$–$C_{10}$)aryl;
  when $R'_1$ represents methyl, $L_1$, $L_2$, $L_3$, $L_4$ and $L_5$ represent a hydrogen atom and R' represents ethyl, then $L_6$ is not isopropyl;

and the salts thereof with a pharmaceutically acceptable acid.

The compounds of formula (I.1) are linear phosphonates.
The compounds of formula (I.2) are cyclic phosphonates.

In the context of the invention, the expression "alkyl" means a linear or branched saturated hydrocarbon radical such as methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl or 1-methyl-1-ethylpropyl.

The alkyl radical preferably contains 1 to 10 and better still 1 to 6 carbon atoms.

The term "alkoxy" denotes the —O-alkyl radical in which alkyl is as defined above.

"Halogen" denotes a chlorine, bromine, fluorine or iodine atom, fluorine and chlorine being preferred.

According to the invention, the term "cycloalkyl" denotes saturated, monocyclic or polycyclic, preferably monocyclic or bicyclic, carbocycles.

Cycloalkyls containing 3 to 8 endocyclic carbon atoms are more particularly preferred.

Cycloalkyls which may be mentioned are cyclobutyl, cyclopentyl, cyclohexyl, cycloheptyl and cyclooctyl, cyclopentyl and cyclohexyl being preferred.

The term "aryl" means a monocyclic or polycyclic, preferably monocyclic or bicyclic, aromatic hydrocarbon radical containing from 6 to 10 endocyclic carbon atoms, such as phenyl and naphthyl.

Among the linear compounds of formula (I.1), the ones which are preferred are those corresponding to one or more of the following conditions:

1) $R_3$ is other than a hydrogen atom.
2) $R_1$ and $R_2$ are both other than a hydrogen atom.
3) $R_3$ represents n-propyl or a linear ($C_5$–$C_6$)alkyl group, optionally substituted with one or more radicals chosen from nitro, halogen, ($C_1$–$C_6$)alkoxy and ($C_3$–$C_8$) cycloalkyl. $R_3$ preferably represents n-propyl or a linear ($C_5$–$C_6$)alkyl group.
4) $R_1$ and $R_2$ independently represent a ($C_1$–$C_6$)alkyl group optionally substituted with one or more radicals chosen from ($C_1$–$C_6$)alkoxy, ($C_5$–$C_6$)cycloalkyl, halogen, ($C_6$–$C_{10}$)aryl and nitro; or alternatively a ($C_6$–$C_{10}$)aryl group optionally substituted with one or more radicals chosen from ($C_1$–$C_6$)alkyl, ($C_1$–$C_6$) alkoxy, halogen, nitro and ($C_5$–$C_6$)cycloalkyl; and R represents a ($C_1$–$C_6$)alkyl group or a ($C_6$–$C_{10}$)aryl group. Advantageously, $R_1$ and $R_2$ independently represent ($C_1$–$C_6$)alkyl or ($C_6$–$C_{10}$)aryl, for example phenyl.
5) R represents a ($C_1$–$C_6$)alkyl group or a ($C_6$–$C_{10}$)aryl group.
6) $R_1$ and $R_2$ do not represent ($C_1$–$C_{18}$)alkyl.
7) At least one from among $R_1$ and $R_2$ represents a deuterium atom, a halogen atom, nitro or optionally substituted ($C_1$–$C_{18}$)alkoxy.

Linear compounds of formula (I.1) that are particularly preferred are:
2-(propylamino)-2-(diethoxyphosphoryl)propane
N-[1-phenyl-1-(diethoxyphosphoryl)ethyl]-N-propylamine.

Among the cyclic compounds of formula (I.2), the ones that are preferred are those in which R' is chosen from ($C_1$–$C_{18}$)alkyl and ($C_6$–$C_{10}$)aryl.

Another group of compounds that are preferred consists of the compounds of formula (I.2) in which $R'_1$ represents ($C_1$–$C_6$)alkyl or a hydrogen atom and $R'_2$ and $R'_3$ together form a radical of formula:

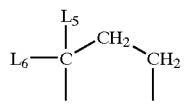

in which $L_5$ and $L_6$ are as defined above.

This group of compounds is denoted hereinbelow as the subgroup PC.

When, in this subgroup of preferred compounds, PC, $R'_1$ represents ($C_1$–$C_6$)alkyl, it is preferable for $R'_2$ and $R'_3$ together to form a divalent radical:

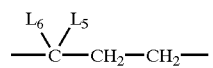

in which $L_5$ represents H and $L_6$ represents ($C_6$–$C_{10}$)aryl, for example phenyl.

When, in the subgroup PC, $R'_1$ represents a hydrogen atom, it is preferable for $R'_2$ and $R'_3$ together to form a divalent radical:

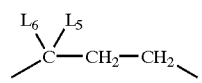

in which $L_5$ represents H and $L_6$ represents —P(O)(OR')$_2$ in which R' is as defined above.

Among all these compounds, those in which R' represents a ($C_1$–$C_6$)alkyl group or a ($C_6$–$C_{10}$)aryl group are particularly preferred.

A marked preference is given to the following cyclic compounds:
2,5-bis(diethoxyphosphoryl)pyrrolidine; and 2-methyl-2-diethoxyphosphoryl-5-phenyl-pyrrolidine.

The invention covers both the cis and trans isomers of the cyclic derivatives, as well as all the enantiomers and diastereoisomers in the case in which the compounds of formula (I.1) or (I.2) contain one or more asymmetric carbons.

According to another of its aspects, the invention relates to the use of aminophosphonates as pH markers in $^{31}$P NMR.

More generally, the invention relates to the use, as pH markers, of compounds of formula (II.1) or (II.2) or of salts thereof with pharmaceutically acceptable acids:

Formula (II.1)

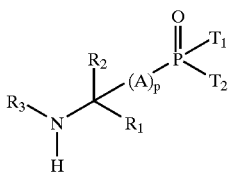

in which $T_1$ and $T_2$ independently represent a group —R or —OR;

R represents a $(C_1-C_{18})$alkyl or $(C_6-C_{10})$aryl group;

$R_1$ and $R_2$ independently represent a hydrogen atom; a deuterium atom; a halogen atom; a $(C_1-C_{18})$alkyl group optionally substituted with one or more radicals chosen from $(C_1-C_6)$alkoxy, $(C_3-C_{11})$cycloalkyl, halogen, $(C_6-C_{10})$aryl and nitro; a $(C_6-C_{10})$aryl group optionally substituted with one or more radicals chosen from $(C_1-C_6)$alkyl, $(C_1-C_6)$alkoxy, halogen, nitro and $(C_3-C_{11})$cycloalkyl; $(C_1-C_{18})$alkoxy optionally substituted with one or more radicals chosen from $(C_1-C_6)$ alkoxy, halogen, nitro, $(C_3-C_{11})$cycloalkyl and $(C_6-C_{10})$aryl; a nitro group; a group —P(O)(OR')$_2$; or a $(C_3-C_{11})$cycloalkyl group optionally substituted with one or more radicals chosen from $(C_1-C_6)$alkyl, $(C_1-C_6)$alkoxy, halogen and nitro;

$R_3$ represents a hydrogen or deuterium atom; a $(C_1-C_{18})$ alkyl group optionally substituted with one or more radicals chosen from nitro, halogen, $(C_1-C_6)$alkoxy, $(C_6-C_{10})$aryl and $(C_3-C_{11})$cycloalkyl, and optionally bearing a group —P(O)(OR)$_2$ in position 1; a $(C_3-C_{11})$ cycloalkyl group optionally substituted with one or more radicals chosen from $(C_1-C_6)$alkyl, $(C_1-C_6)$ alkoxy, halogen and nitro, a $(C_6-C_{10})$aryl group optionally substituted with one or more radicals chosen from $(C_1-C_6)$alkyl, $(C_6-C_{10})$aryl, $(C_1-C_6)$alkoxy, nitro, halogen and $(C_3-C_{11})$cycloalkyl;

p represents 0 or 1;

A represents a divalent radical —CR$_4$R$_5$— in which: R$_4$ and R$_5$ have the meanings given above for R$_1$ and R$_2$ with the exclusion of —P(O)(OR)$_2$;

it being understood that the said compound does not contain more than two groups —P(O)(OR)$_2$.

Formula (II.2)

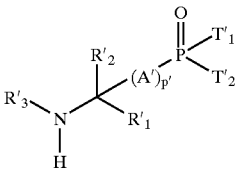

in which $T'_1$ and $T'_2$ independently represent $(C_1-C_{18})$alkyl; $(C_6-C_{10})$aryl; or a group —OR'; R' represents a hydrogen atom or a $(C_1-C_{18})$alkyl or $(C_6-C_{10})$aryl group; $R'_1$ represents a hydrogen atom; a deuterium atom; a halogen atom; a $(C_1-C_{18})$alkyl group optionally substituted with one or more radicals chosen from $(C_1-C_6)$alkoxy, $(C_3-C_{11})$ cycloalkyl, halogen, $(C_6-C_{10})$aryl and nitro; a $(C_6-C_{10})$aryl group optionally substituted with one or more radicals chosen from $(C_1-C_6)$alkyl, $(C_1-C_6)$alkoxy, halogen, nitro and $(C_3-C_{11})$cycloalkyl; $(C_1-C_{18})$alkoxy optionally substituted with one or more radicals chosen from $(C_1-C_6)$alkoxy, halogen, nitro, $(C_3-C_{11})$cycloalkyl and $(C_6-C_{10})$aryl; a nitro group; a group —P(O)(OR')$_2$; or a $(C_3-C_{11})$cycloalkyl group optionally substituted with one or more radicals chosen from $(C_1-C_6)$alkyl, $(C_1-C_6)$alkoxy, halogen and nitro; $R'_2$ and $R'_3$ together form a divalent radical:

(a)

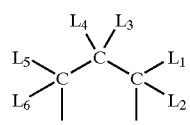

in which the group —C(L$_1$)(L$_2$)— is directly linked to the carbon bearing $R'_1$ and in which $L_1$, $L_2$, $L_3$ and $L_4$ represent, independently of each other, a hydrogen atom; a deuterium atom; a $(C_1-C_{18})$alkyl group optionally substituted with one or more radicals chosen from $(C_1-C_6)$alkoxy, $(C_3-C_{11})$cycloalkyl, halogen, $(C_6-C_{10})$aryl and nitro; a $(C_6-C_{10})$aryl group optionally substituted with one or more radicals chosen from $(C_1-C_6)$alkyl, $(C_1-C_6)$alkoxy, halogen, nitro and $(C_3-C_{11})$cycloalkyl; $(C_1C_{18})$alkoxy optionally substituted with one or more radicals chosen from $(C_1-C_6)$ alkoxy, halogen, nitro, $(C_3C_{11})$cycloalkyl and $(C_6-C_{10})$ aryl; a nitro group; a group —P(O)(OR')$_2$; or a group $(C_3-C_{11})$cycloalkyl optionally substituted with one or more radicals chosen from $(C_1-C_6)$alkyl, $(C_1-C_6)$ alkoxy, halogen and nitro; and $L_5$ and $L_6$ represent, independently of each other, a hydrogen atom; a deuterium atom; a $(C_1-C_{18})$alkyl group optionally substituted with one or more radicals chosen from $(C_1-C_6)$ alkoxy, $(C_3-C_{11})$cycloalkyl, halogen, $(C_6-C_{10})$aryl and nitro; a $(C_6-C_{10})$aryl group optionally substituted with one or more radicals chosen from $(C_1-C_6)$alkyl, $(C_1-C_6)$alkoxy, halogen, nitro and $(C_3-C_{11})$cycloalkyl; $(C_1-C_{18})$alkoxy optionally substituted with one or more radicals chosen from $(C_1-C_6)$alkoxy, halogen, nitro, $(C_3-C_{11})$cycloalkyl and $(C_6-C_{10})$aryl; a nitro group; a group —P(O)(OR')$_2$;

or a $(C_3-C_{11})$cycloalkyl group optionally substituted with one or more radicals chosen from $(C_1-C_6)$alkyl, $(C_1-C_6)$alkoxy, halogen and nitro; or a group —P(O) (OR')$_2$;

p' represents 0 or 1;

A' represents a divalent radical —CR'$_4$R'$_5$— in which R'$_4$ and R'$_5$ have the meanings given above for R'$_1$ with the exclusion of —P(O)(OR')$_2$, it being understood that the said compound does not contain more than two groups —P(O)(OR')$_2$.

The compounds of formula (I.1) above are a subgroup of the compounds of the formula (II.1).

One of the meanings of $R_3$ is n-propyl or linear ($C_5$–$C_{18}$) alkyl, optionally bearing a group —P(O)(OR)$_2$ in position 1. This means that the carbon atom of the n-propyl group or of the ($C_5$–$C_{18}$)alkyl group which is directly linked to the nitrogen atom can bear a group —P(O)(OR)2, as illustrated below:

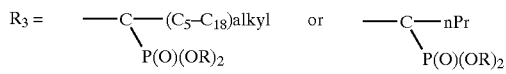

Similarly, the compounds of formula (I.2) above are a subgroup of the compounds of formula (II.2).

According to one preferred embodiment of the invention, the pH marker used is a linear phosphonate corresponding to one or more of the conditions (i) to (xi) below:

i) a compound of formula (II.1) in which $R_3$ is other than a hydrogen atom;

ii) a compound of formula (II.1) in which $R_1$ and $R_2$ are both other than a hydrogen atom;

iii) a compound of formula (II.1) in which p represents 0;

iv) a compound as defined in iii) for which $R_3$ represents a ($C_1$–$C_6$)alkyl group optionally substituted with one or more radicals chosen from nitro, halogen, ($C_1$–$C_6$) alkoxy, ($C_6$–$C_{10}$)aryl and ($C_3$–$C_8$)cycloalkyl, and optionally bearing a group —P(O)(OR)$_2$ in position 1;

v) a compound as defined in iii) for which $R_1$ and $R_2$ independently represent a ($C_1$–$C_6$)alkyl group optionally substituted with one or more radicals chosen from ($C_1$–$C_6$)alkoxy, ($C_5$–$C_6$)cycloalkyl, halogen, ($C_6$–$C_{10}$) aryl and nitro; a ($C_6$–$C_{10}$)aryl group optionally substituted with one or more radicals chosen from ($C_1$–$C_6$) alkyl, ($C_1$–$C_6$)alkoxy, halogen, nitro and ($C_5$–$C_6$) cycloalkyl or alternatively a group —P(O)(OR)$_2$; and R represents a ($C_1$–$C_6$)alkyl group or a ($C_6$–$C_{10}$)aryl group;

vi) a compound as defined in iii) for which $R_3$ represents ($C_1$–$C_6$)alkyl; $R_1$ and $R_2$ independently represent ($C_1$–$C_6$)alkyl or phenyl optionally substituted with one or more ($C_1$–$C_6$)alkyl, ($C_1$–$C_6$)alkoxy, halogen, nitro and ($C_5$–$C_6$)cycloalkyl radicals; or alternatively a group —P(O)(OR)$_2$;

vii) a compound chosen from 2-(propylamino)-2-(diethoxyphosphoryl)propane, N-[1-phenyl-1-(diethoxyphosphoryl)ethyl]-N-propylamine and N-[1,1-bis(diethoxyphosphoryl)methyl]-N-tert-butylamine;

viii) a compound of formula (II.1) in which p represents 1; $R_3$ represents ($C_1$–$C_6$)alkyl; A represents —CR$_4$R$_5$—; $R_1$, $R_2$, $R_4$ and $R_5$ are independently chosen from a hydrogen atom and a ($C_1$–$C_6$)alkyl group; and R represents a ($C_1$–$C_6$)alkyl group or a ($C_6$–$C_{10}$)aryl group;

ix) N-[(1-methyl-2-diethoxyphosphoryl)ethyl]-N-n-butylamine; and ethyl [1-tert-butylamino-2,2-(dimethyl)propyl][methyl]phosphinate;

x) a compound of formula (II.1) in which $T_1$ represents —OR and $T_2$ represents —R;

xi) a compound of formula (II.1) in which $T_1$ and $T_2$ represent —OR.

According to another preferred embodiment of the invention, a cyclic phosphonate of formula (II.2) is used, corresponding to one or more of the conditions (xii) to (xvii) below:

xii) compound of formula (II.2) in which R' is other than a hydrogen atom;

xiii) a compound of formula (II.2) in which R'$_1$ represents a hydrogen atom, a ($C_1$–$C_6$)alkyl group, ($C_6$–$C_{10}$)aryl group or a group —P(O)(OR')$_2$ and R'$_2$ and R'$_3$ together form a radical of formula:

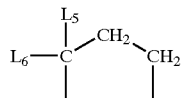

in which $L_5$ and $L_6$ are as defined for formula (II.2);

xiv) a compound as defined in xi) in which $L_5$ and $L_6$ are chosen independently from a hydrogen atom, a ($C_1$–$C_6$) alkyl group, a ($C_6$–$C_{10}$)aryl group or a group —P(O) (OR')$_2$, $R_1$ representing a ($C_1$–$C_6$)alkyl group, a ($C_6$–$C_{10}$)aryl group or a hydrogen atom;

xv) a compound chosen from:
—N-[(1-methyl-2-diethoxyphosphoryl)ethyl]-N-n-butylamine;

2-methyl-2-diethoxyphosphorylpyrrolidine;

2,2-bis(diethoxyphosphoryl)pyrrolidine;

2,2-bis(diisopropoxyphosphoryl)pyrrolidine;

trans-2,5-bis(diethoxyphosphoryl)pyrrolidine;

2-phenyl-2-diethoxyphosphorylpyrrolidine;

2-methyl-2-diethoxyphosphoryl-5-phenylpyrrolidine; and ethyl 2-methylpyrrolidin-2-yl methyl phosphinate;

xvi) a compound of formula (II.2) in which T'$_1$ represents —OR' and T'$_2$ is ($C_1$–$C_{18}$)alkyl or ($C_6$–$C_{10}$)aryl;

xvii) a compound of formula (II.2) in which T'$_1$ and T'$_2$ represent —OR'.

The use of the preferred compounds of formula (I.1) and (I.2) above forms another preferred embodiment of the invention.

In a particularly advantageous manner, the compounds used as pH markers are those of formula (II.2) comprising two functions —P(O)(OR')$_2$ (which form a preferred subgroup of the invention), and more specifically the compounds of formula (II.2) in which:

either $R_1$ represents —P(O)(OR')$_2$;

or $L_5$ or $L_6$ represents —P(O)(OR')$_2$.

The following preparation processes allow the synthesis of the compounds of formulae (II.1) and (II.2) and thus of the compounds of formulae (I.1) and (I.2).

A) The compounds of formula (II.2) for which p' represents 0; T'$_1$ and T'$_2$ represent —OR'; and R'$_2$ and R'$_3$, taken together, form a radical:

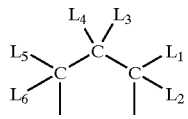

in which $L_1$ to $L_6$ are as defined in formula (II.2) and comprise in their molecule only one function —P(O)(OR')$_2$, can be prepared by reacting a compound of formula (III):

(III)

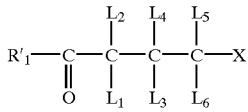

in which $R'_1$, $L_1$, $L_2$, $L_3$, $L_4$, $L_5$ and $L_6$ are as defined for formula (II.2) and X represents a halogen atom such as a chlorine, bromine or iodine atom, with a compound of formula (IV):

(IV)

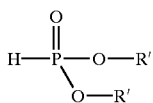

in which R' is as defined for formula (II.2), in the presence of $NH_3$.

The reaction conditions depend on the nature of the reagents of formulae (III) and (IV) and may readily be determined by a person skilled in the art. The reaction is generally carried out in a solvent, for example a polar protic solvent. The solvent is advantageously ethanol. The temperature is generally maintained between room temperature and the reflux temperature of the solvent.

The compounds of formulae (III) and (IV) are commercially available compounds or compounds that can readily be prepared by a person skilled in the art starting with commercially available compounds.

This process is illustrated in patent application FR 93/08906.

B) As a variant, the compounds of formula (II.2) targeted in paragraph A) above and for which $R'_1$ does not represent H, can be prepared by the action of a pyrroline of formula (V):

(V)

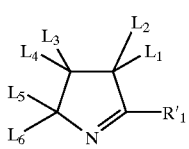

in which $R'_1$, $L_1$, $L_2$, $L_3$, $L_4$, $L_5$ and $L_6$ are as defined above for (II.2), on a compound (IV) of formula:

(IV)

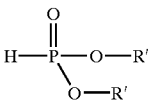

in the presence of a Lewis acid of formula $MX_n$ in which X is a halogen atom, M is an element chosen from B, Al, Fe, Ga, Sb, Sn, As, Zn and Hg and n is an integer between 2 and 5 whose value corresponds to the valency of the element M in the compound $MX_n$. $MX_n$ preferably represents $BF_3$, this acid generally being used in the form of its $BF_3$—$Et_2O$ complex.

The reaction can be carried out at room temperature in a polar aprotic solvent such as an ether, and for example tetrahydrofuran or diethyl ether. A 10 mol % to 50 mol % excess of the compound of formula (IV) is preferably reacted with the pyrroline (V).

The pyrroline of formula (V) can be prepared according to the reaction scheme below:

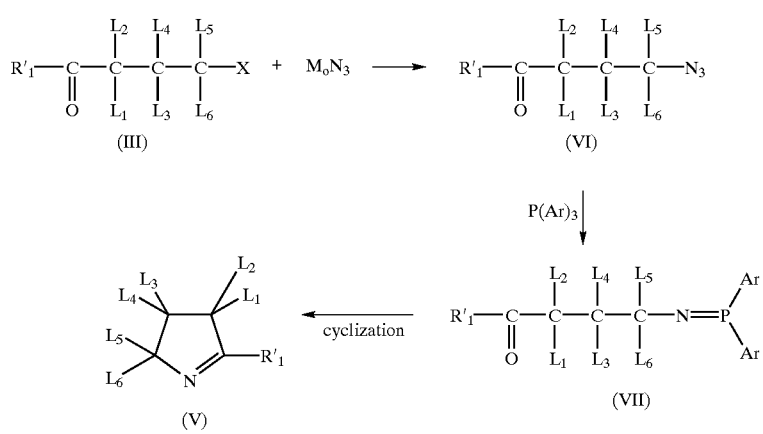

in which $R'_1$ and $L_1$ to $L_6$ are as defined for the formula (II), $M_0$ represents an alkali metal and in particular sodium or potassium; X represents a halogen atom; and Ar represents a $C_6$–$C_{10}$ aromatic group optionally substituted with a $C_1$–$C_6$ alkyl group.

According to this reaction scheme, the compound of formula (III) is reacted with an alkali metal azide of formula $M_0N_3$ in which $M_0$ represents an alkali metal. $M_0N_3$ is preferably $NaN_3$ and the reaction is carried out in a polar aprotic solvent in the presence of an ammonium chloride such as tetrabutylammonium chloride. An example of a solvent which may be mentioned is dimethoxyethane.

As a guide, 1 to 3 molar equivalents of sodium azide are reacted with the derivative of formula (III), preferably 1 to 2 molar equivalents.

The reaction of the resulting compound of formula (VI) with the triarylphosphine of formula $P(Ar)_3$ in which Ar denotes an optionally substituted $(C_6–C_{10})$ aromatic radical is generally carried out in a polar aprotic solvent, preferably diethyl ether. Ar advantageously represents phenyl. The reaction is stoichiometric. The process is preferably performed in the presence of an excess of $P(Ar)_3$.

The cyclization takes place at room temperature after adding a solvent, for instance a hydrocarbon such as pentane to the reaction medium. This reaction is continued for the time required, occasionally for 36 hours; reaction for 5 to 15 hours is generally required. Whatever the case, a person skilled in the art may vary the temperature and the solvent, in a manner which is known per se, to improve the reaction kinetics.

C) The compounds of formula (II.2) targeted in paragraph A) above, in which $L_6$ represents a hydrogen atom, can also be prepared by reducing the corresponding nitrones of formula (VIII):

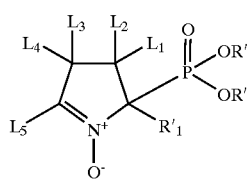

(VIII)

A reducing agent which will be used, for example, is tributyltin hydride or NaHTe. In this respect, a person skilled in the art will refer to D. H. R. Barton et al. (1985), Tetrahedron Letters, 26, 4603.

Patent application FR 93/08906 describes a general method for preparing the compounds of formula (VIII).

As a variant, the compounds of formula (VIII) in which $L_2$, $L_4$ and $L_6$ represent a hydrogen atom and $R'_1$ is other than a hydrogen atom can be prepared by carrying out the following sequence of reaction steps:

in which $R'_1$, $L_1$, $L_3$, $L_5$ and $R'$ are as defined for (II).

The reaction of compound (IX) with compound (X) is advantageously carried out in a polar aprotic solvent such as acetonitrile in the presence of a base such as triethylamine, pyridine or 4-dimethylaminopyridine in catalytic amount. The reaction temperature is generally between room temperature and the reflux temperature of the solvent.

The resulting compound of formula (XI) is reacted with excess zinc in the presence of acetic acid at a temperature of between 0° C. and 100° C., to give the expected compound (VIII).

This reaction can be carried out in a solvent. In this case, a polar protic solvent such as ethanol will preferably be chosen.

The amount of zinc is advantageously between 1 and 5 molar equivalents relative to compound (IX), preferably between 1 and 3 equivalents.

The compound of formula (X) is readily prepared (i) by reacting acetyl chloride with a trialkyl phosphite of formula $P(OR')_3$ according to the Arbuzov method, and then (ii) reacting the resulting dialkyl 2-oxoethylphosphonate with hydroxylamine and (iii) oxidizing the resulting oxime into 1-nitroethylphosphonate (X). The latter oxidation reaction is described in particular in Zon et al., Synthesis, 1984, 661–663 and uses meta-chloroperbenzoic acid as oxidizing agent. This set of steps is reported below:

$CH_3COCl+P(OR')_3 \rightarrow CH_3COP(O)(OR')_2+R'Cl$ $CH_3COP(O)(OR')_2+NH_2OH \rightarrow CH_3C\!=\!N(OH)\!-\!P(O)(OR')_2$ $CH_3C\!=\!N(OH)\!-\!P(O)(OR')_2 \rightarrow CH_3CH(NO_2)\!-\!P(O)(OR')_2$ in which R' is as defined for formula (II.2).

D) The compounds of formula (II.2) for which p' represents 0; $T'_1$ and $T'_2$ represent —OR'; and $R'_2$ and $R'_3$, taken together, form a radical:

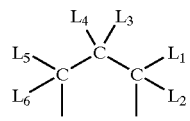

in which $L_1$ to $L_6$ are as defined in formula (II.2) and $R'_1$ represents —$P(O)(OR')_2$, can be prepared from the corresponding 2-oxopyrrolidines of formula (XII):

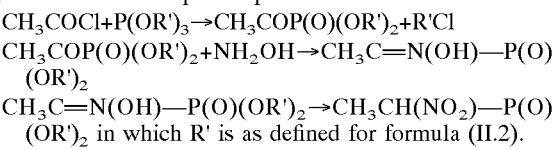

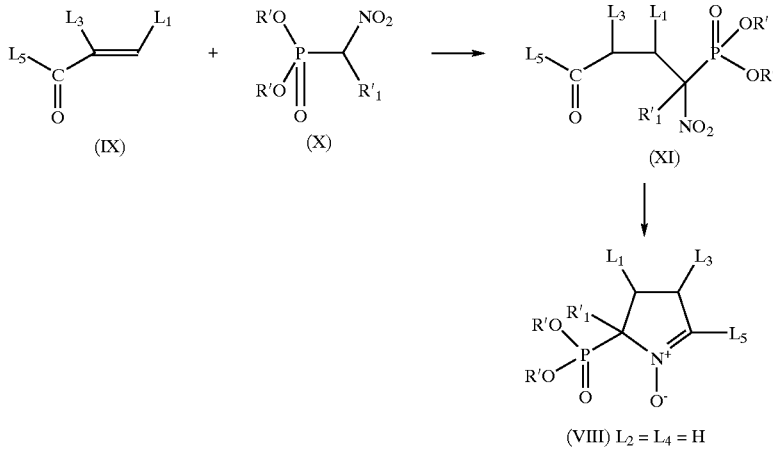

(VIII) $L_2 = L_4 = H$

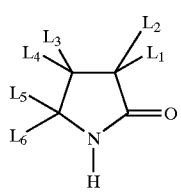

(XII)

in which $L_1$ to $L_6$ are as defined for formula (II).

According to this process, the 2-oxopyrrolidine (XII) is successively reacted with' the appropriate trialkyl phosphite of formula $P(OR')_3$ in which R' is as defined for formula (II), under an inert atmosphere, at a temperature ranging between −10° C. and room temperature, and then with a phosphoryl halide of formula $P(O)X_3$ in which X represents a halogen atom, at this same temperature. According to a preferred embodiment, the reaction mixture is kept stirring while optionally allowing the temperature to rise to room temperature for 1 to 10 hours. The reaction mixture is then treated in a second step with ammonium hydroxide. At least two molar equivalents (relative to the amount of compound (XII)) of $P(OR')_3$ and of $P(O)X_3$ are required for this reaction.

E) The compounds of formula (II.2) in which p' represents 0; $T'_1$ and $T'_2$ represent —OR'; and $R'_2$ and $R'_3$, taken together, form a radical:

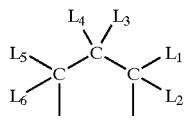

in which $L_1$ to $L_5$ and $R'_1$ are as defined in formula (II.2), and $L_6$ represents —$P(O)(OR')_2$, can be prepared according to following reaction scheme:

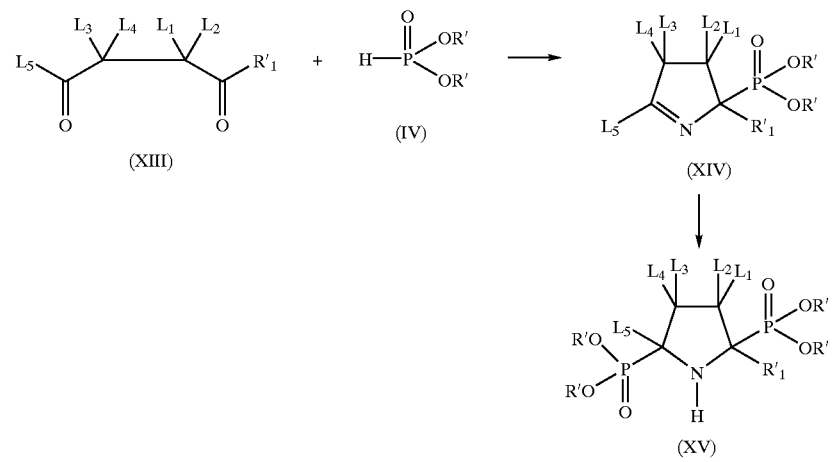

According to one preferred embodiment, the reaction of (XIII) with (IV) is carried out in the presence of a large excess of compound (XIII): from 5 to 20 molar equivalents of compound (XIII) give satisfactory yields. The reaction takes place in the presence of ammonia at a temperature between room temperaature and 100° C., preferably between 20° C. and 70° C. In a second step, the resulting compound of formula (XIV) is reacted with compound (IV), preferably with an excess of the compound of formula (IV). The molar ratio of compound (XIV) to compound (IV) is generally between 10:1 and 2:1, preferably between 5:1 and 2:1.

F) The linear compounds of formula, (II.1) in which p represents 0 and $T_1$ and $T_2$ represent —OR are prepared simply by addition of an amine of formula (XVI):

 (XVI)

in which $R_3$ is as defined for the formula (II), to a ketone of formula (XVII):

 (XVII)

in which $R_1$ and $R_2$ are as defined for formula (II), in the presence of a compound of formula (IV):

 (IV)

in which R is as defined for formula (II). This reaction is stoichiometric but can be carried out in the presence of an excess of the amine (XVI) and/or of the phosphite (IV). The molar ratio of the amine (XVI) to the ketone (XVII) preferably ranges between 0.2 and 2 and better still between 0.8 and 1.8. The molar ratio of the phosphite (IV) to the ketone (XVII) preferably ranges between 0.3 and 2 and better still between 0.5 and 1.5.

The reaction can be carried out without solvent or in the presence of a solvent. Preferably, the reagents are used as solvents. The temperature is maintained between 200° C. and 500° C. The reaction is advantageously carried out at room temperature.

According to one specific embodiment, the amine (XVI) is reacted at room temperature with the ketone (XVII) in the presence of an alkali metal sulphate and a strong acid, such as the system $Na_2SO_4/HCl$. In this case, a mixture of the ketone (XVII) and the amine (XVI) is prepared and the Na₂SO₄/HCl system is added thereto. After a reaction time of between 1 and 72 hours, the phosphite (IV) is added to the reaction mixture.

From 0.5 to 2 equivalents of alkali metal sulphate and a catalytic amount of the strong acid are preferably used. The alkali metal is chosen from sodium, potassium, lithium and caesium, sodium being preferred.

G) The linear compounds of the formula (II.1) in which p represents 0; $T_1$ and $T_2$ represent —OR; and $R_3$ comprises a group —P(O)(OR)₂ can be prepared by adapting the process described by Von K. Issleib in Z. anorg. allg. Chem. 444, 249–255 (1978).

This process is more particularly suitable for synthesizing the compounds of formula (XVIII):

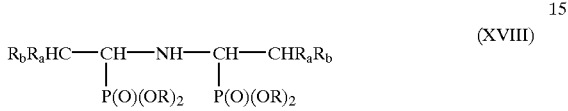

(XVIII)

in which R is as defined for formula (II.1) and $R_a$ and $R_b$ independently represent a ($C_1$-$C_{18}$)alkyl group optionally substituted with one or more radicals chosen from nitro, halogen, ($C_1$-$C_6$)alkoxy, ($C_6$-$C_{10}$)aryl and ($C_3$-$C_8$) cycloalkyl; or alternatively $R_a$ and $R_b$ form, together with the carbon atom which bears them, a ($C_3$-$C_8$)cycloalkyl.

According to this process, an aldehyde of formula $R_aR_bCH$—CHO is treated with ammonia. Thermolysis of the resulting compound gives the dimer of formula:

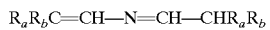

which is reacted at a temperature of between 15° C. and 35° C. with two molar equivalents of the phosphite of formula (IV):

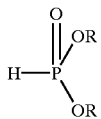

(IV)

in which R is as defined above.

The compounds of formula (XVIII) in which $R_a$ and $R_b$ are chosen independently from ($C_1$-$C_6$)alkyl or form, together with the carbon atom which bears them, a ($C_5$-$C_8$) cycloalkyl group, are prepared in particular by this method.

H) The linear compounds of formula (II.1) in which p represents 0; $T_1$ and $T_2$ represent —OR; and either $R_1$ or $R_2$ represents —P(O)(OR)₂, can be prepared by the action of two molar equivalents of a suitable trialkyl phosphite of formula P(OR)₃ in which R is as defined for (II.1), on a formamide of formula (XIX):

$R_3$—NH—COH (XIX)

in the presence of phosphorus oxychloride POCl₃ at a temperature of between −15° C. and 0° C., preferably between −10° C. and 0° C.

Although 2 molar equivalents of the trialkyl phosphite are generally sufficient, it is possible to use a slight molar excess of phosphite. Thus, the molar ratio of the trialkyl phosphite to compound (XIX) preferably ranges between 2.5 and 2, preferably between 2.2 and 2.

The reaction is generally carried out by adding POCl₃ to a solution consisting of the mixture of the trialkyl phosphite and the formamide, maintained at −5° C.

The molar amount of POCl₃ used in this reaction ranges between 2 and 2.5 mol per 1 mol of the compound (XIX).

The molar ratio of POCl₃ to the trialkyl phosphite preferably ranges between 1 and 1.3.

I) The linear compounds of formula (II.1) in which p represents 1 and either $R_1$ or $R_2$ represents a hydrogen atom, can be prepared by carrying out the process which follows:

In a first step, the trialkyl phosphite of formula P(OR)₃ in which R is as defined for formula (II.1) is reacted with a chloride of formula (XX)

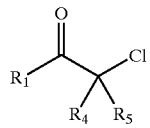

(XX)

at a temperature of between 80° C. and 200° C. This reaction is described more specifically in N. D. Dawson et al., J. Am. Chem. Soc., 74, 5312–5314, 1952. A person skilled in the art will known how to adapt the reaction conditions to the nature of the various reagents placed in contact. This reaction is preferably carried out in the absence of solvent at a temperature of from 140° C. to 180° C. The product resulting from this first step, of formula:

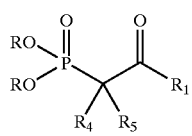

(XXI)

is reacted with an amine of formula $R_3$—NH₂ in the presence of a hydride, preferably in the presence of NaBH (OAc)₃ and of a $C_1$-$C_4$ alkylcarboxylic acid such as acetic acid. This reaction is preferably carried out in the presence of a halogenated hydrocarbon solvent (such as dichloroethane) at a temperature of between 15° C. and 35° C., for example at room temperature (22° C.). After this reaction, the desired compound of formula (II) is obtained.

The reactions used in these two steps are stoichiometric. Equivalent molar amounts of phosphite P(OR)₃ and of chloride (XX), and respectively of the compound (XXI) and of the amine $R_3$—NH₂, will thus be placed in contact. In the second step, the molar ratio of the alkylcarboxylic acid to the compound (XXI) may range between 1 and 5, preferably between 1 and 2. Moreover, the molar ratio of the hydride to the compound (XXI) will be adjusted to between 1 and 1.5, preferably between 1 and 1.2.

J) The compounds of general formula (II.2) in which p' represents 1; $T'_1$ and $T'_2$ represent —OR'; and $R'_2$ and $R'_3$, taken together, form a radical

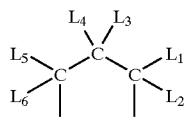

in which $L_1$ to $L_6$ are as defined in formula (II.2) and comprising in their molecule only one function —P(O)(OR')₂, can be prepared:

(i) by reacting a compound of formula (XXII)

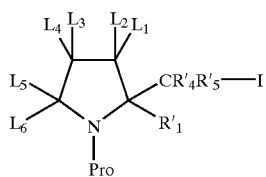
(XXII)

in which $L_1$ to $L_6$, $R'_1$, $R'_4$ and $R'_5$ are as defined above and Pro represents a protecting group for an amine function, for example a benzyloxycarbonyl group, with a phosphoryl derivative of the formula $P(OR')_3$ in which R' is as defined for formula (II.2); and (ii) by deprotecting the secondary amine function of the product obtained from the first step (i).

This synthetic method is described and illustrated in particular in FR-A-2 707 990.

The protecting functions which can be used to protect the endocyclic nitrogen of the pyrrolidine ring are those conventionally used in organic chemistry. A person skilled in the art will refer, for example, to Protective Groups in Organic Synthesis, Greene T. W. and Wuts P. G. M., published by John Wiley and Sons, 1991. This book also describes the corresponding deprotection methods.

The compounds of formula (XXII) can be prepared in two steps from the compounds of formula (XXIII)

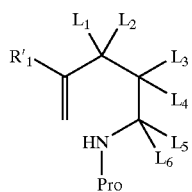
(XXIII)

in which $L_1$ to $L_6$, $R'_1$ and Pro are as defined above for compound (XXII).

In a first step, a compound (XXIII) is reacted with mercury diacetate; the second step, which consists in treating the resulting product successively with potassium iodide and iodine, leads directly to the corresponding compound of formula (XXII).

The compounds of formula (XXIII) are readily prepared by a person skilled in the art using conventional organic chemistry processes, starting with commercially available compounds.

K) The compounds of formula (II.2) as defined in E) in the case where $L_5$ and $R'_1$=H can also be prepared according to the following scheme:

Step 1: Synthesis of Pyrrolidine-2,5-diphosphonic Acid

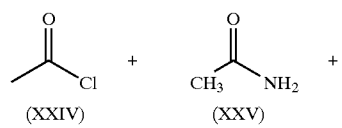
(XXIV)   (XXV)

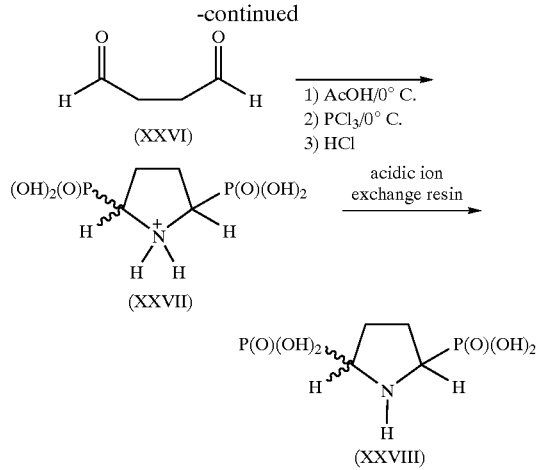
(XXVI)
(XXVII)
(XXVIII)

Step 2: Esterification

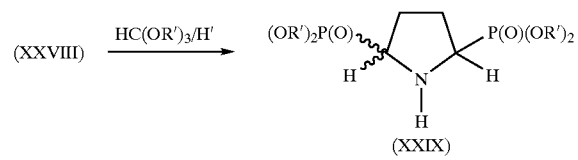
(XXVIII) → (XXIX)

L) The compounds of formula (II.2) in which p'=0 and at least one from among $T_1$ and $T'_2$ represents $(C_1–C_{18})$alkyl or $(C_6–C_{10})$aryl can be prepared according to the following synthetic scheme:

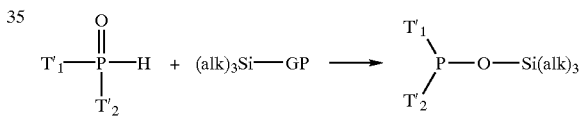
XXXa   XXXI   XXXII

↓

XXXIII

↓

(II.2)

in which $T'_1$, $T'_2$, $R'_1$ and $L_1$ to $L_6$ are as defined in formula (II.2) above; alk represents $(C_1–C_6)$alkyl and GP represents a leaving group, preferably a halogen atom such as chlorine.

The reaction of the phosphinate XXXa with the silyl derivative XXXI is stoichiometric. The molar ratio of compound XXXI to compound XXXa thus generally ranges between 1 and 1.5, preferably between 1 and 1.2.

This reaction is carried out in the presence of a base, preferably an organic base such as a tertiary amine. Suitable bases are N-methylmorpholine, triethylamine, tributylamine, diisopropylamine, dicyclohexylamine, N-methylpiperidine, pyridine, 4-(1-pyrrolidinyl)pyridine, N,N-dimethylaniline and N,N-diethylaniline.

The reaction of XXXa with XXXI is preferably carried out in a polar solvent such as a halogenated aliphatic hydrocarbon such as dichloromethane, carbon tetrachloride or dichloroethane.

The reaction temperature is preferably maintained between −20° C. and 10° C. and better still between −5° C. and 5° C.

In a second step, the compound XXXII obtained is reacted with the appropriate pyrroline of formula XXXIII. This reaction is preferably carried out in situ, without intermediate isolation of the compound XXXII obtained above.

A molar ratio of the pyrroline XXXIII to the silyl derivative XXXII of from 1 to 1.5 and preferably from 1 to 1.2 is generally suitable.

The reaction of XXXIII with XXXII is generally carried out in a polar solvent such as a halogenated aliphatic hydrocarbon as defined above.

This process is particularly suitable for preparing the compounds (II.2) above in which $T'_1$ represents $(C_1-C_{18})$ alkyl or $(C_6-C_{10})$ aryl and $T'_2$ represents —OR'.

M) The compounds of formula (II.1) in which p=0 and at least one from among $T_1$ and $T_2$ represents —R can be prepared in accordance with the following reaction scheme:

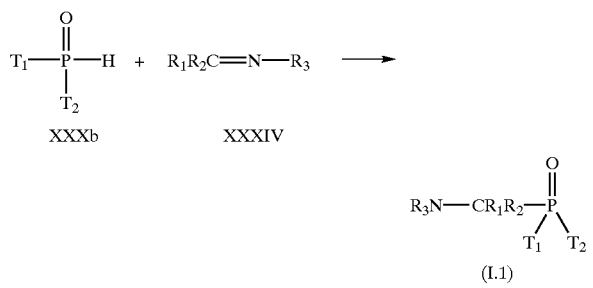

(I.1)

in which $R_1$, $R_2$, $R_3$, $T_1$ and $T_2$ are as defined above in formula (I.1).

This reaction can be carried out in the absence of solvent or in the presence of an inert solvent capable of dissolving the reagents XXXb and XXXIV.

A suitable temperature is a temperature of between 15° C. and 80° C., preferably between 30° C. and 50°0 C.

The compounds of formulae XXXa and XXXb are prepared conventionally according to the standard methods of organic chemistry.

By way of illustration, the phosphinate XXXa (or XXXb respectively) [in which $T_1$ (or $T'_1$ respectively) represents —OR (or OR' respectively) and $T_2$ (or $T'_2$ respectively) represents R (or $(C_1-C_{18})$ alkyl or $(C_6-C_{10})$ aryl respectively)] can be obtained by reacting a halophosphite of formula $(alk_0)(T_1)Phal_1$ (or $(alk_0)(T'_1)Phal_1$ respectively) in which $hal_1$ represents a halogen atom, preferably chlorine, and $alk_0$ represents $(C_1-C_6)$ alkoxy, with a magnesium reagent of formula $T_2Mghal_2$ (or $T'_2Mghal_2$ respectively) in which $hal_2$ is a halogen atom, preferably an iodine atom, followed by reaction of the resulting compound with an ammonium halide, for example ammonium chloride. This reaction sequence can be represented schematically as follows:

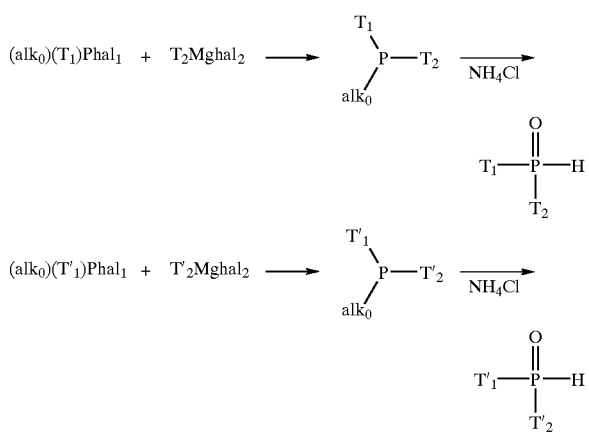

The imine XXXIV is prepared conventionally according to the known methods of organic chemistry and, for example, by the action of an amine on an aldehyde.

The compounds XXXI are commercially available or readily prepared by a person skilled in the art starting with commercially available compounds.

This process is particularly suitable for preparing the compounds (II.1) above in which $T_1$ represents —R and $T_2$ represents —OR.

The compounds of formulae (II.1) and (II.2) (or (I.1) and (I.2) respectively) can be isolated in the form of their salts with an organic or inorganic acid, for example picric acid, oxalic acid, tartaric acid, mandelic acid or camphorsulphonic acid. However, the physiologically acceptable salts are preferred, such as the hydrochloride, hydrobromide, sulphate, hydrogen sulphate, dihydrogen phosphate, maleate, fumarate, 2-naphthalenesulphonate or para-toluenesulphonate.

The originality of the phosphonates of formula (II.2) lies mainly in their rigid cyclic structure.

Among the compounds of formula (II.2), those for which R' is other than a hydrogen atom are preferred.

All the compounds of formula (II.1) (which are linear phosphonates) are such that R is other than a hydrogen atom.

When R' in formula (II.2) and R in formula (II.1) are other than a hydrogen atom, the function(s) —P(O)(OR')$_2$, or —P(O)(OR)$_2$ respectively, are in the form of phosphonate groups.

For all the compounds of the invention, the chemical shift of the phosphorus, in $^{31}P$ NMR, depends on the pH. More specifically, the chemical shift of the phosphorus varies greatly for pH values close to the pKa of the compound of formula (II.1) or (II.2) being investigated. For pH values that are far from the pKa value, the chemical shift of the phosphorus tends towards a constant.

The variation in the chemical shift of the phosphorus (δ) as a function of the pH can be represented schematically in the following way:

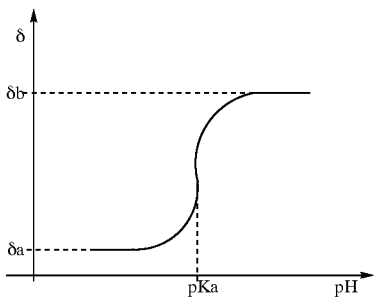

The inventors have found, surprisingly, that when all the functions —P(O)(OR')$_2$ and —P(O)(OR)$_2$ in the compounds of the invention are in the form of phosphonates (R'≠H and R≠H), then the difference $\Delta\delta=\delta_b-\delta_a$ is particularly large. Now, the greater the value of $\Delta\delta$, the greater the pH measurement sensitivity. Thus, the compounds of formulae (II.1) and (II.2) in which R, or R' respectively, is other than a hydrogen atom are particularly sensitive and reliable pH markers.

Whereas the pH markers of the prior art generally show a difference $\Delta\delta$ of 2 to 3 ppm, the compounds of the invention of formulae (II.1) and is (II.2) in which R' is other than a hydrogen atom have a $\Delta\delta$ which is four times as large.

Depending on the nature of the substituents $R_1$, $R_2$ and $R_3$ (or $R'_1$, $R'_2$ and $R'_3$ respectively), the pKa value of the compound of formula (II.1) (or (II.2) respectively) varies. In point of fact, the pKa value depends on the electron-withdrawing or electron-donating effect of these substituents.

When R' represents a hydrogen atom, the family of compounds of formula (II.2) has a rather narrow pKa distribution, compared with the pKa distribution obtained with the corresponding family of compounds of formula (II.2) for which R'≠H.

Similarly, the compounds of the invention of formula (II.1) have a broad distribution of pKa values, compared with the corresponding family of compounds combining the compounds of formula (II.3) below:

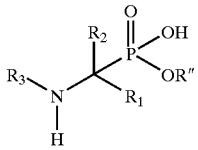

(II.3)

in which $R_1$, $R_2$ and $R_3$ are as defined for formula (II.1) and R" represents H or is as defined above for R in formula (II.1).

More specifically, the compounds of the invention have pKa values of between 2 and 9.

It will be noted that the diphosphoryl compounds, and in particular the cyclic diphosphoryl compounds of formula (II.2), also give a greater $\Delta\delta$ variation.

In order to demonstrate the ability of the compounds of the formulae (I.1), (I.2), (II.1) and (II.2) above to function as pH-markers, the variation in the chemical shift of the $^{31}$P NMR peak as a function of the pH was studied. The results obtained allowed titration curves to be plotted.

The attached FIGS. 1 to 8 are titration curves obtained using the following compounds:

FIG. 1: Titration curve for 2-methyl-2-diethoxyphosphorylpyrrolidine: compound 1

Figure 2:
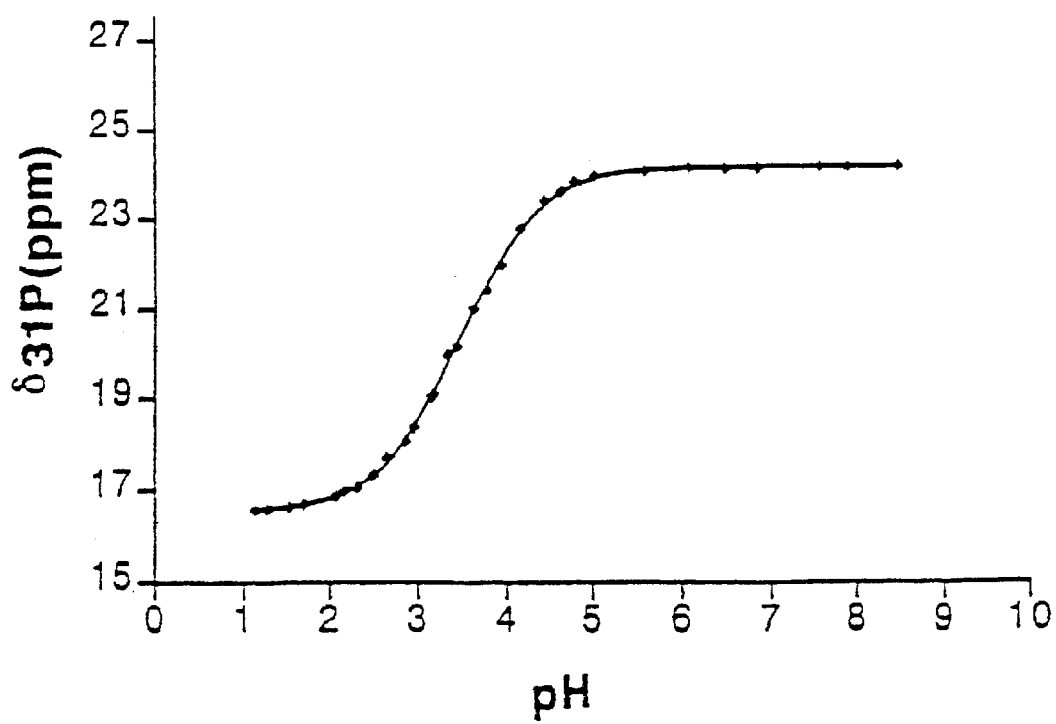

FIG. 2: Titration curve for 2,2-bis(diethoxyphosphoryl) pyrrolidine: compound 2

Figure 3:
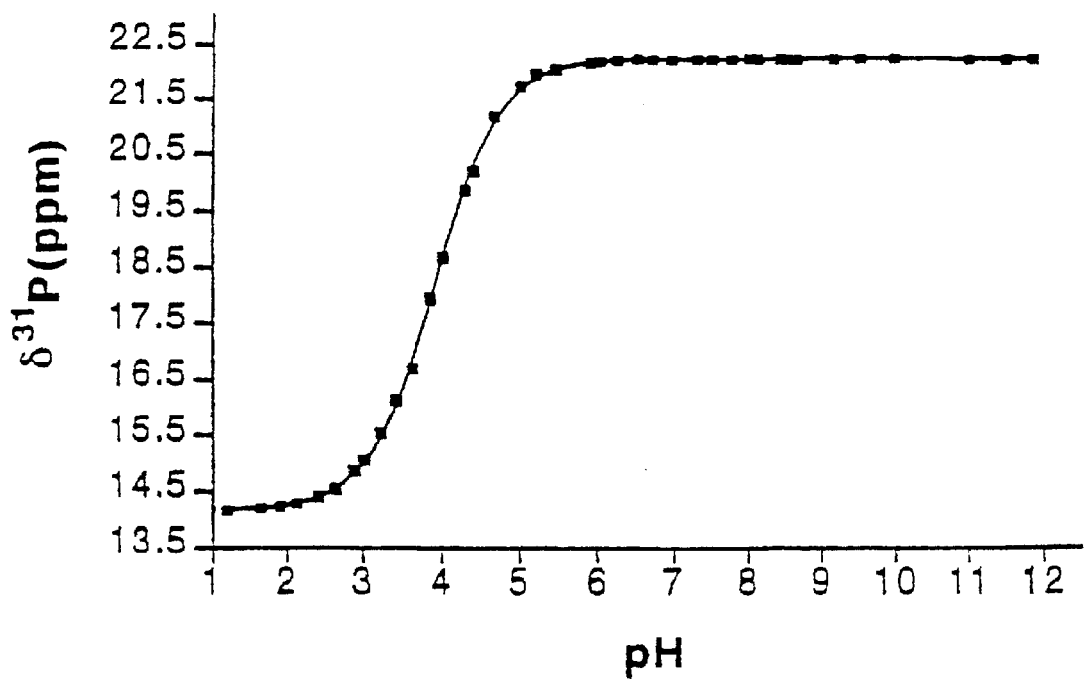

FIG. 3: Titration curve for 2,2-bis(diisopropoxyphosphoryl) pyrrolidine: compound 3

Figure 4:
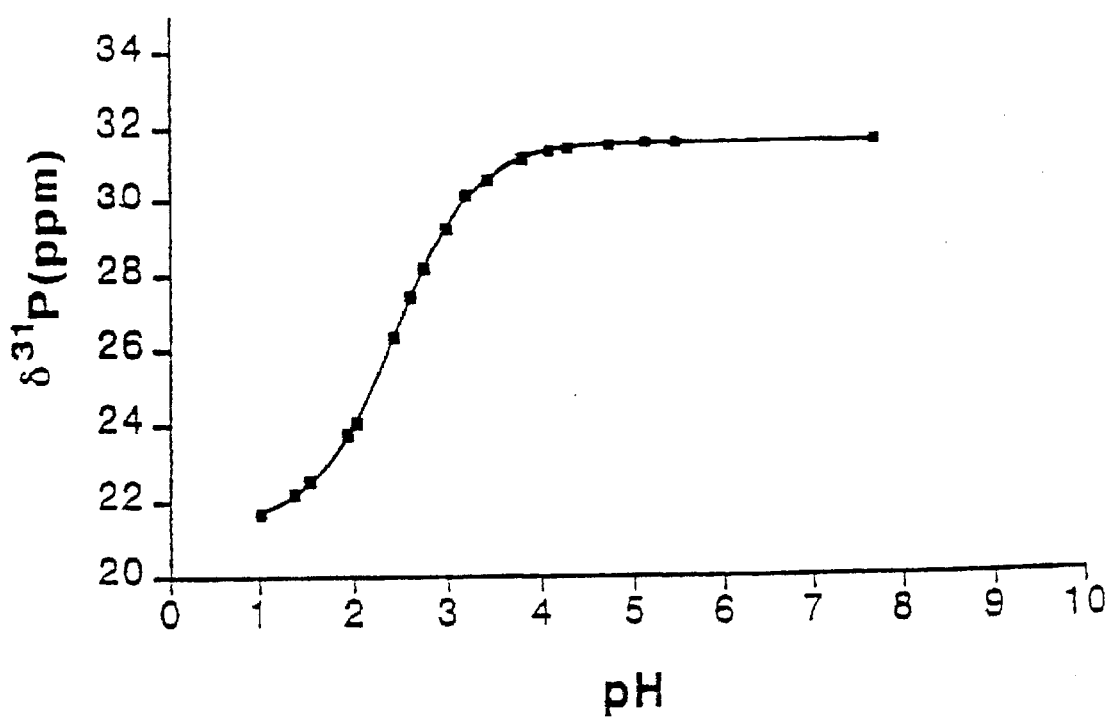

FIG. 4: Titration curve for 2,5-bis(diethoxyphosphoryl)-2,5-dimethylpyrrolidine: compound 4

Figure 5:
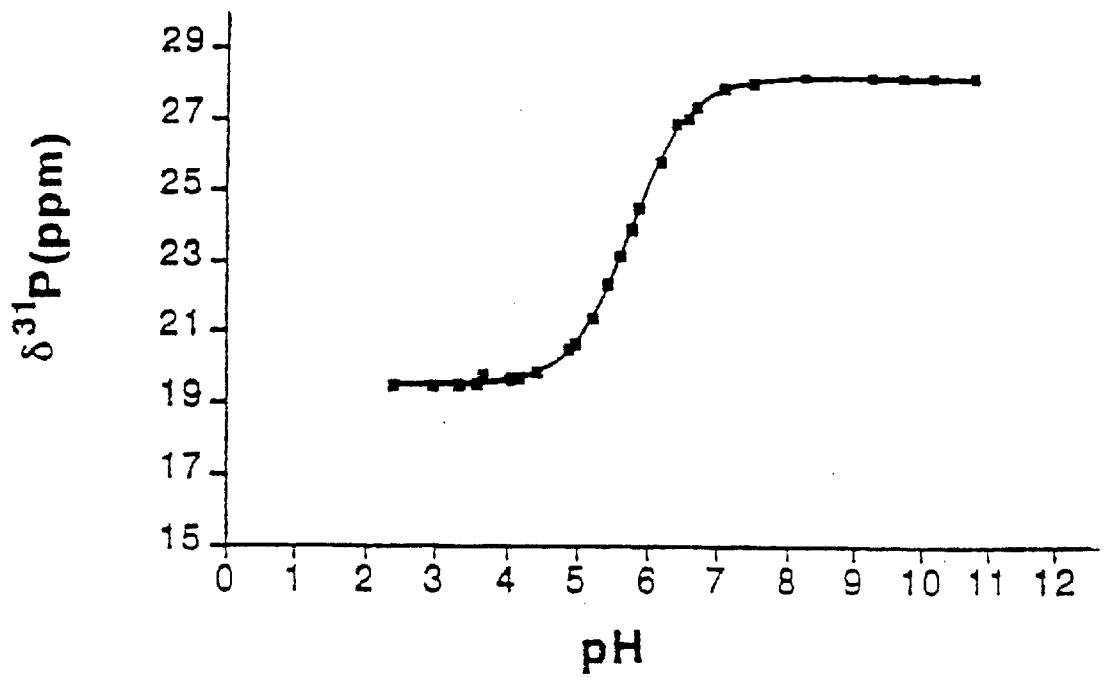

FIG. 5: Titration curve for 2-phenyl-2-diethoxyphosphorylpyrrolidine: compound 5

Figure 6:
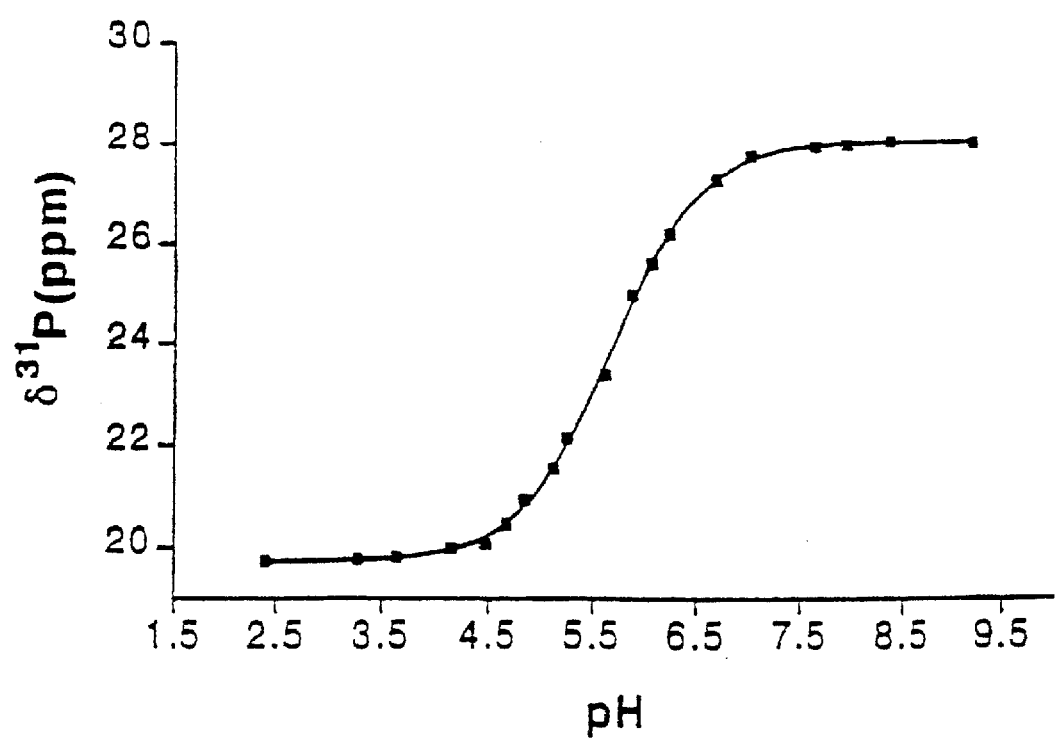

FIG. 6: Titration curve for N-propyl-N-[1-phenyl-1-diethoxyphosphorylethyl]amine: compound 6

Figure 7:
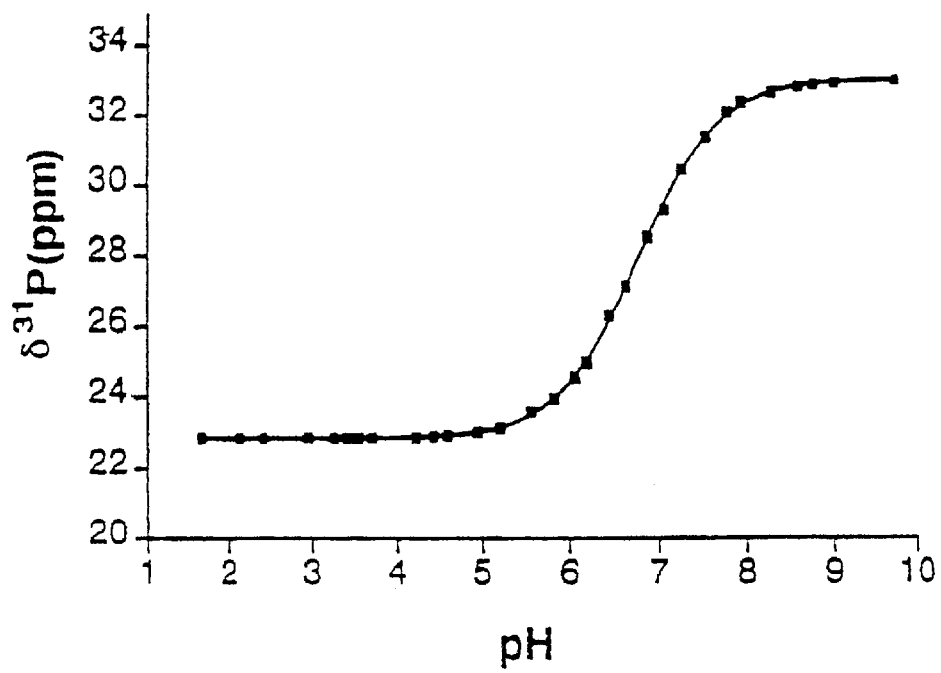

FIG. 7: Titration curve for 2-propylamino-2-diethoxyphosphorylpropane: compound 7

Figure 8:
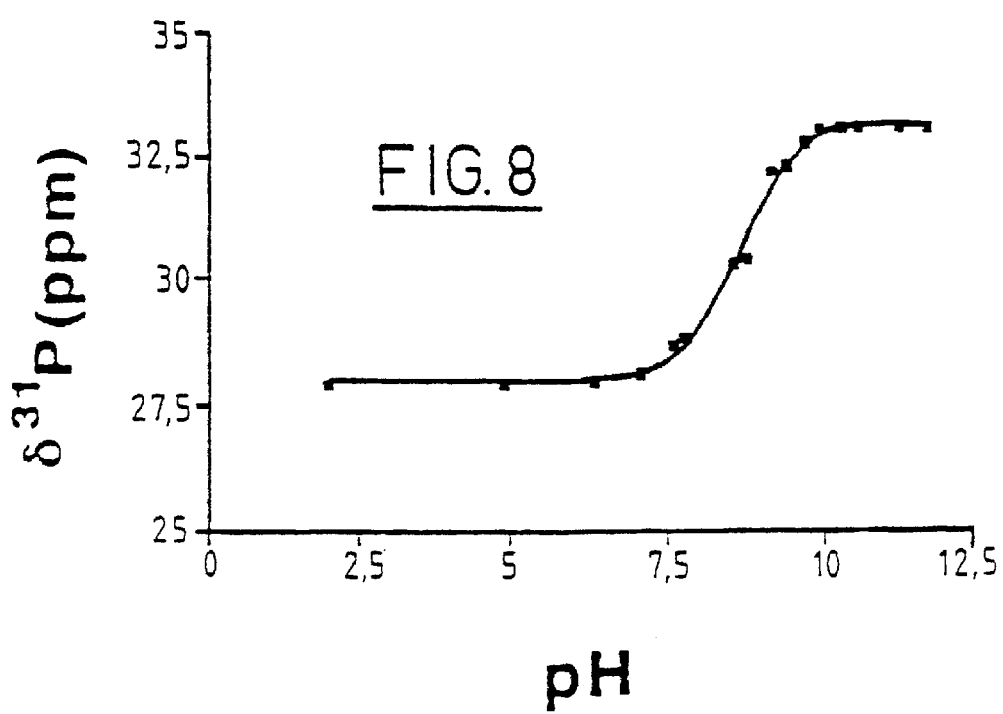

FIG. 8: Titration curve for N-[(1-methyl-2-diethoxyphosphoryl)ethyl]-N-n-butylamine.

Each measurement was taken at 37° C. using a 5 mM solution of the test compound in a phosphate buffer on a 400 MHz NMR spectroscopy machine.

Table 1 below reports the pKa values measured using the curves plotted for each of the test compounds.

TABLE 1

| Compound | 1 | 2 | 3 | 4 | 5 | 6 | 7 | 8 |
|---|---|---|---|---|---|---|---|---|
| PKa | 6.75 | 3.47 | 3.90 | 2.45 | 5.73 | 5.67 | 6.77 | 8.64 |

The pKa values measured show that compounds 1 to 7 allow pH measurements over a very broad pH range. More generally, by modifying the nature of the substituents R, $R_1$, $R_2$, $R_3$, $R'_1$, $R'_2$, $R'_3$ and R' of the compounds of formulae (I.1), (I.2), (II.1) and (II.2), it is possible to provide pH markers that are particularly sensitive in different pH zones, down to the most acidic values, a given compound ensuring good measurement accuracy only in the pH zone surrounding its pKa. This presents a certain advantage over the known pH markers, since the known compounds do not make it possible to study the acidic compartments of cells.

The compounds of formulae (I.1), (I.2), (II.1) and (II.2) are thus pH markers that are particularly advantageous, offering greater accuracy in the measurement of intracellular pH.

It is confirmed that the diphosphoryl compounds give higher NMR sensitivity, thus making it possible to reduce the concentration of marker required.

For comparative purposes, three additional experiments were carried out in order to compare the sensitivity of compound 1 and inorganic phosphate.

The variation in the phosphorus-31 chemical shift was studied as a function of the pH: the measurements were taken at 22° C., or 37° C. respectively, on a 400 MHz NMR machine using 5 mM solutions of the test compound in a phosphate buffer.

Figure 9:
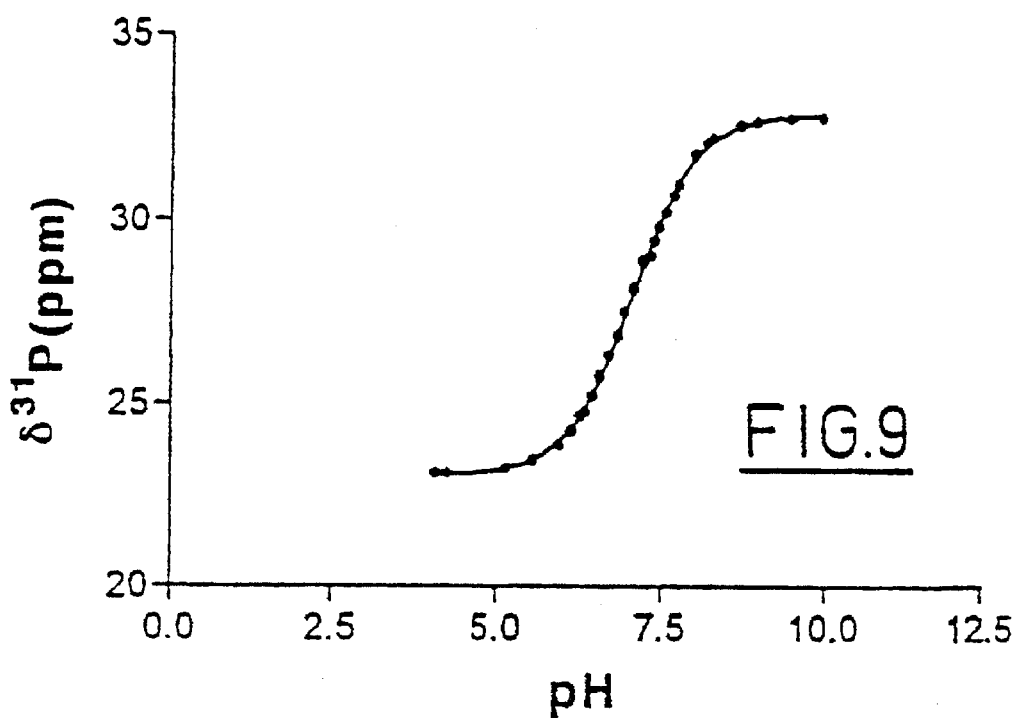
Figure 10:
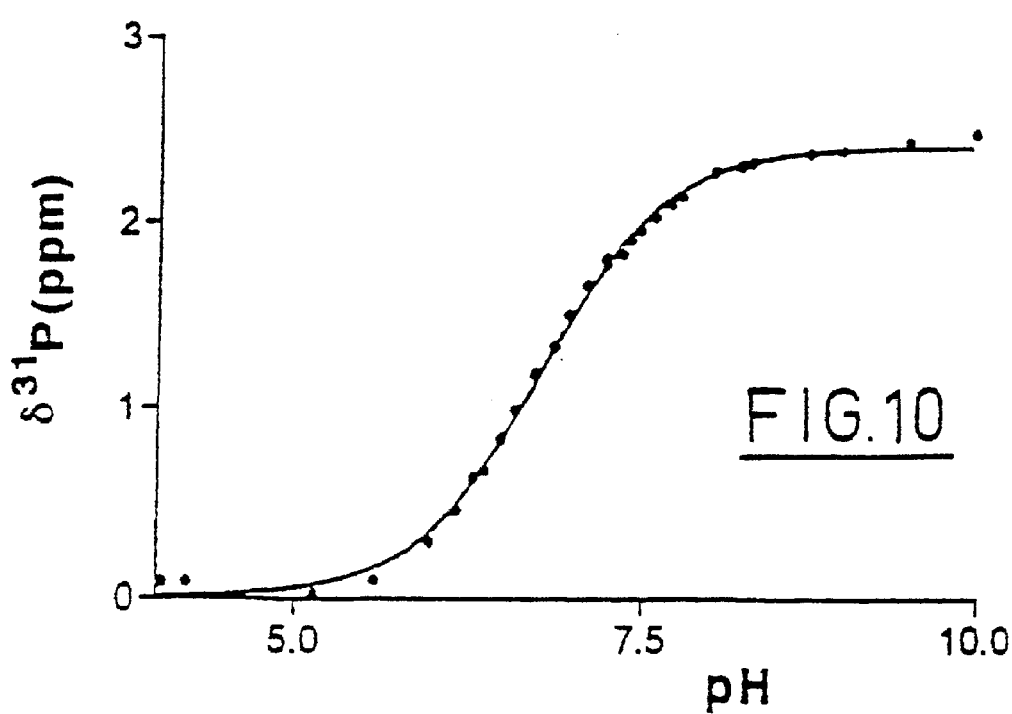
Figure 11:
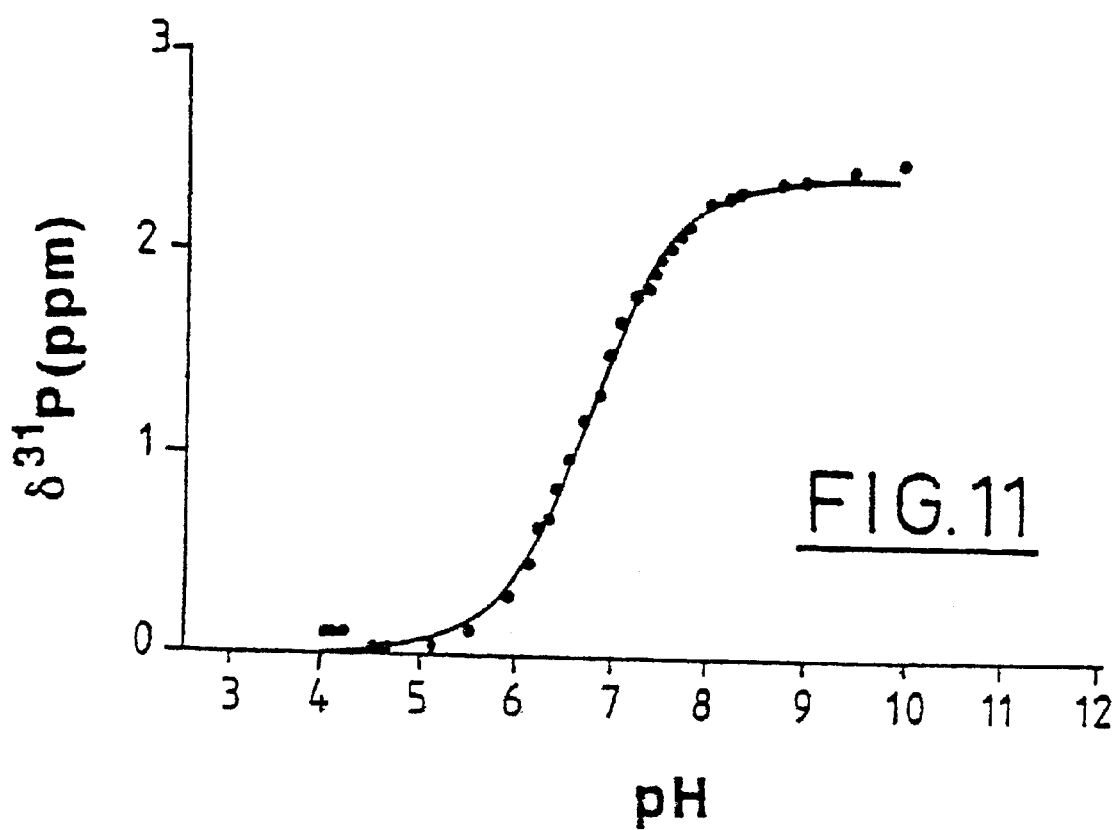

The results obtained are reported in FIGS. 9 to 11:

FIG. 9: Titration curve for compound 1, at 22° C.

FIG. 10: Titration curve for inorganic phosphate, at 22° C.

FIG. 11: Titration curve for inorganic phosphate, at 37° C.

These curves show that when the pH varies between 4 and 10, the chemical shift of the inorganic phosphate peak in $^{31}$P NMR varies between 0.062 and 2.741 at 37° C. (FIG. 11) and between 0.086 and 2.481 at 22° C. (FIG. 10), i.e. by an amplitude of between 2.679 and 2.395 according to the experimental conditions. On the other hand, in the case of compound 1, with the pH varying between 4 and 10, the chemical shift of the phosphorus peak in $^{31}$P NMR varies between 23.185 and 32.834 at 37° C. (FIG. 1) and between 23.137 and 32.779 at 22° C. (FIG. 9), i.e. by an amplitude of between 9.649 and 9.642 according to the experimental conditions.

The pKa values of these various compounds are reported in Table 2 below.

TABLE 2

| Compound | Compound 1 | Pi | Pi |
|---|---|---|---|
| Temperature | 22° C. | 22° C. | 37° C. |
| PKa | 7.06 | 6.75 | 6.65 |

These results demonstrate the higher measurement sensitivity obtained with the compounds of formulae (II.1) and (II.2).

Thus, the superiority of the compounds of formulae (I.1), (I.2), (II.1) and (II.2) over inorganic phosphate is incontrovertible.

The compounds of formulae (II.1) and (II.2) are on the whole particularly non-toxic and penetrate into myocardial or liver cells (in sufficient amount to be observed but in a sufficiently small amount to remain non-toxic), thus allowing a measurement of the pH values of intracellular and extracellular media. Better still, in the case of the liver which possesses very acidic (pH 5) vesicles, the marker 2-diethoxyphosphoryl-2-methylpyrrolidine allows three measurements at the same time: extracellular medium, cytosolic medium (in the case of 2-diethoxyphosphoryl-2-methylpyrrolidine, variations in the chemical shift of the phosphorus as a function of the intracellular acidosis are observed, in the course of ischaemia, which are, for example, fully correlated with those of the intracellular Pi) and intravesicular medium (vesicles whose function is yet to be determined).

Accordingly, the compounds of formulae (II.1) and (II.2) are very powerful tools for enabling a better understanding of the functioning of different cellular organells and the proton fluxes which ensure their functioning.

The following abbreviations have been used in the examples:

| | |
|---|---|
| iPr: | isopropyl |
| n-Bu: | n-butyl |
| CHCl₃: | chloroform |
| bp: | boiling point |
| δ: | chemical shift | s: singlet; d: doublet; t: triplet; dd: doubled doublet; q: quartet; sext.: sextet; m: multiplet; J: coupling constant.

EXAMPLES

Example 1

Synthesis of Compound 1 of Formula

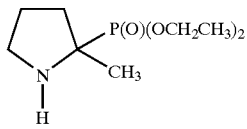

A mixture of 2-methylpyrroline 4 (10.9 g; 0.13 mol) and diethyl phosphite (21.7 g; 0.16 mol) is kept stirring for 7 days at room temperature. After addition of 150 ml of HCl solution (1N), the mixture is then washed with $CH_2Cl_2$ (2×80 ml). The aqueous phase is then basified with sodium carbonate and the product is extracted with $CHCl_3$ (3×100 ml). The organic phase is dried over sodium sulphate and concentrated under reduced pressure. Compound 1 is obtained in the form of a colourless oil (27.30 g; 95%).

IR (KBr, cm$^{-1}$): 3315, 1235, 1055, 1037, 958; $^{31}$P NMR ($C_6D_6$) δ (ppm) 29.6; (CDCl$_3$) δ (ppm) 29.9; $^1$H NMR ($C_6D_6$, 100 MHz) δ (ppm) 1.10 (t, J=7.0 Hz, 6H); 1.28 (d, J=15 Hz, 3H); 1.20–1.80 (m, 3H); 2.00–2.50 (m, 1H); 2.70–3.00 (m, 2H); 3.70–4.50 (m, 4H); $^{13}$C NMR ($C_6D_6$) δ (ppm) 16.63; 16.72; 19.53; 26.08 (d, J=4.5 Hz); 35.18 (d, J=2.5 Hz); 50.35 (d, J=150.7 Hz); 62.05; 62.30 (d, J=7.2 Hz). Elemental analysis: calculated for $C_9H_{20}NO_3P$: C: 48.89; H: 9.11; N: 6.33; Found: C: 48.49; H: 9.15; N: 6.24.

Example 2

Synthesis of Compound 2 of Formula

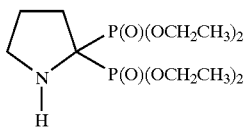

Phosphorus oxychloride (40 ml; 0.44 mol) is added over 1 h 15 min at −5° C. to a solution of 2-pyrrolidinone (18.5 g; 0.22 mol) and triethyl phosphite (9.42 mol). The reaction medium is stirred for 5 hours at room temperature and then poured onto a mixture of ice (300 g) and 32% aqueous ammonia (300 ml). The aqueous phase is extracted with dichloromethane (4×100 ml) and the organic extracts are evaporated under reduced pressure to give a yellow oil. The oil is dissolved in 100 ml of dichloromethane and 200 ml of water are added, followed by addition of 37% hydrochloric acid to pH 1. The aqueous phase is washed with dichloromethane (4×50 ml). Sodium hydroxide and sodium carbonate are added to pH 10 and the aqueous phase is extracted with dichloromethane (4×50 ml). The organic phase is dried over sodium sulphate, filtered and then evaporated under reduced pressure to give the gem-bisphosphonate. 33.4 g of the expected product (47% yield) are thus obtained.

$^1$H NMR (400 MHz, $C_6D_6$) δ (ppm) 1.10 (t, 6H J=7.1 Hz, —O—CH$_2$—C$\underline{H}_3$); 1.11 (t, 6H, J=7.1 Hz, —O—CH$_2$—C$\underline{H}_3$); 1.69 (q, 2H, J=6.8 Hz; $J_{Ha-Hb}$=7.2 Hz, HN—CH$_2$—C$\underline{H}_2$—CH$_2$—C); 2.42 (n, 2H, $J_{Ha-Hb}$=7.2 Hz, $J_{P-H}$=17.7 Hz, HN—CH$_2$—CH$_{2(b)}$—CH$_{2(a)}$—C); 2.88 (t, 2H, J=6.5 Hz, HN—C$\underline{H}_2$—CH$_2$—CH$_2$—C); 4.17 (m, 8H, —O—C$\underline{H}_2$CH$_3$); $^{13}$C (100 MHz); ($C_6D_6$) δ (ppm) 16.5 (t, $J_{C-P}$=7.2 Hz, C$\underline{H}_3$—CH$_2$—OP); 16.6 (t, $J_{C-P}$=5.5 Hz, $\underline{C}H_3$—CH$_2$—O—P—), 26.5 (t, $J_{C-P}$=3.1 Hz, HN—CH$_2$—$\underline{C}H_2$—CH$_2$—C); 31.2 (t, $J_{C-P}$=3.0 Hz, HN—CH$_2$—CH$_2$—C); 47.7 (t, $J_{C-P}$=4.0 Hz, HN—$\underline{C}H_2$—CH$_2$—CH$_2$—C); 62.7 (t, $J_{C-P}$=3.6 Hz, CH$_3$—$\underline{C}H_2$—O—P—); 62.8 (t, $J_{C-P}$=151.8 Hz, HN—CH$_2$—CH$_2$—CH$_2$—$\underline{C}$); 63.4 (t, $J_{C-P}$=5.3 Hz, CH$_3$—$\underline{C}H_2$—O—P—); $^{31}$P (40 MHz; CDCl$_3$) δ 22.5 ppm; IR (without solvent): 3480 (NH); 2982, 2932; 2909; 2869; 1456; 1392; 1243; (P=O); 1164 (P—OC$_2$H$_5$); 1044; 968; 794; 732; 645; 580; 536 cm$^{-1}$ bp: 140° C. (8 Pa) pKa: 3.5 Rf: 0.39 (acetone); 0.43 (dichloromethane/ethanol: 19/1).

Example 3

Synthesis of Compound 3 of Formula

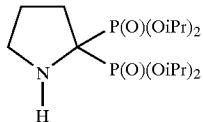

Using a procedure similar to that of Example 2, starting with phosphorus oxychloride, 2-pyrrolidinone and triisopropyl phosphite, 37.2 g of the title compound (45% yield) are obtained.

$^1$H NMR (400 MHz; $C_6D_6$) δ (ppm) 1.22 (d, 6H $J_{H-H}$=6.1 Hz, —O—CH(C$\underline{H}_3$)$_2$); 1.27 (d, 6H, $J_{H-H}$=6.4 Hz, —O—CH(C$\underline{H}_3$)$_2$); 1.28 (d, 6H, $J_{H-H}$=6.3 Hz, —O—CH(C$\underline{H}_3$)$_2$); 1.31 (d, 6H, $J_{H-H}$=6.2 Hz, —O—CH(CH$_3$)$_2$); 1.75 (q, 2H, J=6.8 Hz, $J_{H-H}$=6.9 Hz, HN—CH$_2$—C$\underline{H}_2$—CH$_2$—C); 2.37 (tt, 2H, $J_{H-H}$=7.3 Hz, $J_{P-H}$=17.7 Hz, HN—CH$_2$—CH$_2$—C$\underline{H}_2$—C); 2.95 (t, 2H, J=6.5 Hz, HN—C$\underline{H}_2$—CH$_2$—CH$_2$-C); 4.87 (m, 1H, —O—C$\underline{H}$(CH$_3$)$_2$); 5.00 (m, 1H, —O—CH(CH$_3$)$_2$); $^{13}$C (100 MHz; $C_6D6$) δ (ppm) 23.8 (t, $^3J_{C-P}$=6.7 Hz, —O—CH(C$\underline{H}_3$)$_2$); 24.0 (t, $^3J_{C-P}$=6.4 Hz, —O—CH(C$\underline{H}_3$)$_2$); 24.4 (s, —O—CH(C$\underline{H}_3$)$_2$); 24.7 (s, —O—CH(C$\underline{H}_3$)$_2$); 26.4 (t, $^3J_{C-P}$=3.3 Hz, HN—CH$_2$—C$\underline{H}_2$—CH$_2$—C); 31.0 (t, $^2J_{C-P}$=3.4 Hz, HN—CH$_2$—CH$_2$—C$\underline{H}_2$—C); 47.7 (t, $^3J_{C-P}$=4.6 Hz, HN—C$\underline{H}_2$—CH$_2$—CH$_2$—C); 63.1 (t, $^2J_{C-P}$=151.1, NH—CH$_2$—CH$_2$—CH$_2$—$\underline{C}$); 70.8 (t, $^2J_{C-P}$=6.7 Hz, —O—$\underline{C}$H(CH$_3$)$_2$); 71.7 (t, $^2J_{C-P}$=6.2 Hz, —O—CH(CH$_3$)$_2$); $^{31}$P (40 MHz; CDCl$_3$) δ 21.2 ppm; Elemental analysis: calculated for $C_{16}H_{35}NO_6P_2$:

|  | C | H | N |
|---|---|---|---|
| Calculated (%) | 48.12 | 8.83 | 3.51 |
| Found (%) | 48.21 | 8.80 | 3.51 |

Example 4

Synthesis of Compound 5 of Formula

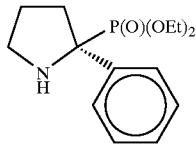

a) 2-Phenylpyrroline 14 g of chlorobutyrophenone (0.078 mol) and 1.5 equivalents of sodium azide (7.6 g; 0.117 mol) in 60 ml of dimethoxyethane are mixed with 0.5 g of tetrabutylammonium chloride in a 250 ml two-necked round-bottomed flask equipped with a condenser, under an inert atmosphere.

The mixture is maintained at 75° C. on an oil bath for 16 hours. The reaction mixture is filtered through Celite. After extraction with ethyl ether and evaporation of the solvent under reduced pressure, 16.2 g of crude product are obtained in the form of a dark oil. This oil was not purified.

The crude product is taken up with 200 ml of anhydrous ethyl ether in a 500 ml three-necked round-bottomed flask, to which is added 20.4 g of triphenylphosphine (0.777 mol) in several portions. This results in an evolution of nitrogen, which may be observed by installing a guard tube. 100 ml of pentane are then added and the mixture is left at room temperature for 12 hours under magnetic stirring. The triphenylphosphine oxide precipitated is filtered off on a sinter funnel. After evaporation of the solvents under reduced pressure, 12.5 g of crude product are obtained. The pyrroline is recrystallized from pentane.

$^1$H NMR: (100 MHz, CDCl$_3$, TMS) 7.9–7.8 (m, 2H); 7.4–7.3 (m, 3H); 4.1–4 (tt, 2H); 2.9–2.8 (tt, 2H); 2.1–1.9 (m, 2H).

b) 2-Phenyl-2-diethoxyphosphorylpyrrolidine 1.2 equivalents of diethyl phosphite are added to 12.5 g of the pyrroline prepared in a) over 24 hours and 1 ml of the diethyl ether/trifluoroborane catalyst in ethyl ether, with magnetic stirring.

The reaction mixture is treated with 0.1 N hydrochloric acid solution until a pH of 1 is obtained. The aqueous phase thus obtained is treated with sodium hydroxide solution until a pH of 8 is obtained. The treatment is completed by addition of Na$_2$CO$_3$ and the mixture is then saturated with NaCl. The resulting mixture is extracted again with dichloromethane (4×30 ml). The organic phase is dried over MgSO$_4$. After evaporation of the solvents under reduced pressure, 9.8 g of crude product (45% yield) are obtained in the form of a yellow oil. The phosphite is evaporated under reduced pressure. The pyrrolidine is purified by chromatography on silica with acetone/pentane (1/3) as eluent, in a yield of 60%.

$^{31}$P ($C_6D_6$) δ 26.9 ppm; $^1$H NMR: (400 MHz, $C_6D_6$): 0.92 (3H, t, OCH$_2$CH$_3$, $^3J_{HH}$=7.07 Hz); 0.97 (3H, t, OCH$_2$CH$_3$, $^3J_{HH}$=7.07 Hz); 1.45–1.34 (1H, m, CH); 1.69–1.58 (1H, m, CH); 2.24–2.15 (1H, m, CH); 2.49 (1H, broad s, NH); 2.63–2.51 (1H, m, CH); 2.79 (1H, dd, CH): 3.0–2.94 (1H, m, CH); 3.85–3.67 (2H, m, OCH$_2$CH$_3$); 3.94–3.87 (2H, m, OCH$_2$CH$_3$); 7.11–7.06 (1H, m, H$_{ar}$); 7.24–7.20 (2H, m, H$_{ar}$); 7.83–7.79 (2H, m, H$_{ar}$). $^{13}$C (100.6, MHz, $C_6D_6$): 16.78 and 16.83 (OCH$_2$$\underline{C}$H$_3$); 25.94 (CH$_2$(3), J=9.05 Hz); 37.33 (CH$_2$(2) ); 47.22 (CH$_2$(4), J=9.05 Hz); 62.66 and 63.04 (O$\underline{C}$H$_2$CH$_3$, J 7.0 Hz): 67.7 (Ph—$\underline{C}_1$—P, J=149.9 Hz); 127.41 (CH(8), J=3.0 Hz); 128.36 (CH(6), J=3.0 Hz); 128.49 (CH(7), J=4.01 Hz); 142.7 C(5).

Example 5

Synthesis of Compound 6 of Formula

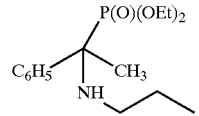

3.45 g of benzophenone (0.029 mol; 1 eq.) 2.8 g of n-propylamine (0.047 mol; 1.6 eq.), 2 drops of concentrated hydrochloric acid and 4.3 g of Na$_2$SO$_4$ (0.03 mol; 1 eq.) are introduced into. a reactor under magnetic stirring. After stirring for 3 days at room temperature, 4.83 g of diethyl phosphite (0.035 mol: 1.2 eq.) are added to the reaction mixture. After stirring for 10 days at room temperature, an acid-base treatment is carried out in order to obtain the expected compound. The yield is 51%.

Example 6

Synthesis of Compound 7 of Formula

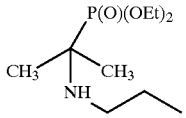

24 g of acetone (0.4 mol; 1 eq.), 28 g of diethyl phosphite (0.2 mol; 0.5 eq.) and 25 g of n-propylamine (0.42 mol; 1 eq.) are introduced into a reactor under magnetic stirring. The mixture is left to react for 3 days at room temperature and an acid-base treatment is carried out in order to obtain the expected compound, which has a boiling point of 70° C. at 0.06 mbar. Yield=66%.

Example 7

Synthesis of 2,5-bis(Diethoxyphosphoryl)-2,5-dimethylpyrrolidine (Compound 4)

Step 1

Preparation of Diethyl (2,5-dimethyl-1-pyrrolin-5-yl)phosphonate

Hexane-2,5-dione (25.68 g; 0.225 mol) and diethyl phosphite (22.48 g; 0.163 mol) are placed in a 500 ml three-necked round-bottomed flask equipped with a condenser and a magnetic stirrer. Ammonia is then bubbled through at a temperature of 35° C. for 21 hours. The reaction mixture is then treated with 0.1 M HCl solution to pH=1, after which it is extracted with diethyl ether. The aqueous phase obtained is treated by addition of NaHCO$_3$ to pH=10. The amine is salted out by adding NaCl and a large excess of Na$_2$CO$_3$ with stirring, in the presence of diethyl ether. The aqueous phase is then extracted with diethyl ether, after which the organic phase is dried over anhydrous Na$_2$SO$_4$. After filtration and evaporation under vacuum, the expected compound is obtained in the form of a yellow oil (12.95 g; 34%).

$^{31}$P NMR (40.53 MHz, CDCl$_3$) 27.59 ppm $^1$H NMR: (100 MHz, CDCl$_3$); 1.32 ppm (6H; t; J$_{H-H}$=6.98 Hz; C$\underline{H}_3$—CH$_2$); 1.48 ppm (3H; d; J$_{H-P}$=16.29 Hz; C$\underline{H}_3$—C—P); 2.07 ppm (3H; d; J$_{H-P}$=4.65 Hz; C$\underline{H}_3$—C=N); between 2.5 and 2.8 ppm (4H; m; C$\underline{H}_2$—CH$_2$); 4.15 ppm (4H; dq; J$_{H-H}$=J$_{H-P}$=6.98 Hz; CH$_3$—C$\underline{H}_2$); $^{13}$C NMR: (25.18 MHz, CDCl$_3$): 16.39 ppm (d; J$_{C-P}$=7.25 Hz; $\underline{C}$H$_3$—CH$_2$); 19.64 ppm (d' J$_{C-P}$=2.9 Hz; $\underline{C}$H$_3$—C=N); 23.48 ppm (s; $\underline{C}$H$_3$—C—P); 32.37 ppm (d; J$_{C-P}$=3.73 Hz; $\underline{C}$H$_2$—CH$_2$); 39.59 ppm (s; $\underline{C}$H$_2$—CH$_2$); 62.45 ppm (d; J$_{C-P}$=7.43 Hz; $\underline{C}$H$_2$—CH$_3$); 177.32 ppm (d; J$_{C-P}$=13.62 Hz; $\underline{C}$=N)

Step 2

Preparation of 2,5-bis(Diethoxyphosphoryl)-2,5-dimethylpyrrolidine

Diethyl 2,5-dimethyl-1-pyrrolin-5-yl)phosphonate prepared in step 1 above (4.87 g; 0.0208 mol) is placed in a 250 ml two-necked round-bottomed flask and diethyl phosphite (5.89 g; 0.043 mol) is added dropwise thereto. The reaction is stirred at room temperature for 5 days. The reaction mixture is treated with 0.1 M HCl solution to pH=1 and is then extracted with diethyl ether. The aqueous phase obtained is: treated by addition of NaHCO$_3$ to pH=10. The amine is salted out by adding NaCl and a large excess of Na$_2$CO$_3$ with stirring, in the presence of diethyl ether. The aqueous phase is then extracted with diethyl ether, after which the organic phase is dried over anhydrous Na$_2$SO$_4$. After filtration and evaporation under vacuum, the title compound is obtained in the form of an orange oil (3.41 g, 44%).

$^{31}$P NMR (40.53 MHz, CDCl$_3$): 29.23 ppm; $^1$H NMR: (100 MHz, CDCl$_3$); 1.33 ppm (6H; t; J$_{H-H}$=6.78 Hz; C$\underline{H}_3$—CH$_2$); 2.16 ppm (6H; d; J$_{H-P}$=1.13 Hz; CH$_3$—C—P): between 2 and 2.5 ppm (4H; m; C$\underline{H}_2$—CH$_2$); 4.18 ppm (4H; dq; J$_{H-H}$=J$_{H-P}$=6.78 Hz; CH$_3$—C$\underline{H}_2$) $^{13}$C NMR: (25.18 MHz, CDCl$_3$): 16.34 ppm (d; J$_{C-P}$=6.57 Hz; $\underline{C}$H$_3$—CH$_2$); 24.42 ppm (d; J$_{C-P}$=4.45 Hz; $\underline{C}$H$_3$—C—P); 34.26 ppm (s; $\underline{C}$H$_2$); 54.55 ppm (d; J$_{C-P}$=150 Hz; N—C—P); 61.95 ppm (d; J$_{C-P}$=6.82 Hz; $\underline{C}$H$_2$—CH$_3$)

Example 8

Synthesis of the Compound of Formula

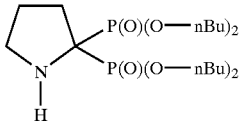

Using a procedure similar to that of Example 2, starting with phosphorus oxychloride, 2-pyrrolidinone and tri-n-butyl phosphite, 23.2 g of the title compound (47% yield) are obtained.

$^1$H NMR: (400 MHz; C$_6$D$_6$) δ (ppm) 0.82 (t, 6H, J=7.4 Hz, —O—CH$_2$—CH$_2$—CH$_2$—C$\underline{H}_3$); 0.83 (t, 6H, J=7.4 Hz, —O—CH$_2$—CH$_2$—CH$_2$—C$\underline{H}_3$); 1.32 (sext. 4H, J=7.3 Hz, —O—CH$_2$—CH$_2$—C$\underline{H}_2$—CH$_3$); 1.33 (sext. 4H, J: 7.5 Hz, —O—CH$_2$—CH$_2$—C$\underline{H}_2$—CH$_3$); 1.56 (m, 8H, —O—CH$_2$—C$\underline{H}_2$—CH$_2$—CH$_3$); 1.76 (q, 2H, J=6.9 Hz, J$_{H-H}$=7.2 Hz, HN—CH$_2$—C$\underline{H}_2$—CH$_2$—C); 2.49 (n, 2H, J$_{Ha-Hb}$=7.3 Hz, J$_{P-H}$=17.8 Hz, HN—CH$_2$—CH$_{2(b)}$—CH$_{2(a)}$—C); 2.97 (t, 2H, J=6.5 Hz, HN—C$\underline{H}_2$—CH$_2$—CH$_2$—C); 4.22 (m, 4H, —O—C$\underline{H}_2$—CH$_2$—CH$_2$—CH$_3$); 4.27 (m, 4H, —O—C$\underline{H}_2$—CH$_2$—CH$_2$—CH$_3$); 5.30 (s, 1H, $\underline{H}$N—); $^{13}$C (100 MHz; C$_6$D$_6$) δ (ppm) 14.1 ($\underline{C}$H$_3$—CH$_2$—CH$_2$—CH$_2$—O—P); 19.4 (CH$_3$—$\underline{C}$H$_2$—CH$_2$—CH$_2$—O—P); 26.8 (t, J$_{C-P}$=3.2 Hz, HN—CH$_2$—$\underline{C}$H$_2$—CH$_2$—C); 31.5 (t, J$_{C-P}$=3.0 Hz, HN—CH$_2$—CH$_2$—$\underline{C}$H$_2$—C); 33.4 (t, J$_{C-P}$=2.7 Hz, CH$_3$—CH$_2$—$\underline{C}$H$_2$—CH$_2$—O—P); 33.5 (t, J$_{C-P}$=2.7 Hz, CH$_3$—CH$_2$—$\underline{C}$H$_2$—CH$_2$—O—P); 48.1 (t, J$_{C-P}$=4.3 Hz, HN—$\underline{C}$H$_2$—CH$_2$—CH$_2$—C); 63.2 (t, J$_{C-P}$=152.0 Hz, HN—CH$_2$—CH$_2$—CH$_2$—$\underline{C}$); 67.1 (t, J$_{C-P}$=3.5 Hz, CH$_3$—CH$_2$—$\underline{C}$H$_2$—O—P); 67.8 (t, J$_{C-P}$=3.2 Hz, CH$_3$—CH$_2$—$\underline{C}$H$_2$—O—P) $^{31}$P (40 MHz; CDCl$_3$): δ 22.7 ppm.

Example 9

Preparation of the Compound of Formula

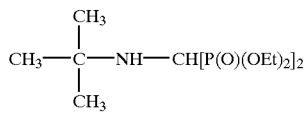

Triethyl phosphite (23 g; 0.14 mol) and N-tert-butylformamide (7.5 g; 0.073 mol) are placed in a 250 ml two-necked round-bottomed flask. The compounds are mixed together at room temperature for a few minutes. An ice bath with salt is installed and at −5 °C., 23 g of POCl$_3$ (i.e. 0.15 mol) are added. The addition takes 1 hour. The reaction is then left stirring at room temperature for 5 hours. The solution gradually turns orange. The crude mixture is then poured into a beaker containing 150 g of ice and 150 ml of 32% aqueous ammonia solution. The aqueous phase is extracted with twice 150 ml of dichloromethane. 100 ml of water are added, followed by dropwise addition of 37% HCl solution until the pH=1. After extraction with 4 times 20 ml of dichloromethane, the aqueous phase is recovered and NaHCO$_3$ is added thereto until the pH=10. After extraction with diethyl ether, drying over Na$_2$SO$_4$ and evaporation of the solvent, the title compound is obtained in the form of a yellowish oil (9.63 g; 56%).

$^{31}$P NMR (40.53 MHz, CDCl$_3$); 20.01 ppm; $^1$H NMR (200 MHz, CDCl$_3$); 1.12 ppm (9H; s; C$\underline{H}_3$—C); 1.35 ppm (12 H; t; J$_{H-H}$=6 Hz: C$\underline{H}_3$—CH$_2$); 2.77 ppm (1H; m; C$\underline{H}$—P); 4.13–4.29 ppm (8 H; m; C$\underline{H}_2$) $^{13}$C NMR (50.32 MHz, CDCl$_3$); 16.10 ppm (m, $\underline{C}$H$_3$—CH$_2$); 29.20 ppm (S; $\underline{C}$H$_3$—C); 48.95 ppm (t; J$_{C-P}$=148.5 Hz; $\underline{C}$H—P); 51.70 ppm (t; J$_{C-P}$=10.5 Hz; $\underline{C}$—N); 62.54 ppm (d; J$_{C-P}$=4 Hz; $\underline{C}$H$_2$); 62.61 ppm (d; J$_{C-P}$=3.5 Hz; $\underline{C}$H$_2$); 63.13 ppm (d; J$_{C-P}$=3.2 Hz); 63.21 ppm (d; J$_{C-P}$=3.85 Hz); Elemental analysis: calculated for C$_{13}$H$_{31}$NO$_6$P$_2$; C: 43.45; H: 8.70; N: 3.90 Found: C: 43.12; H: 8.86; N: 3.58.

Example 10

Synthesis of the Compound of Formula

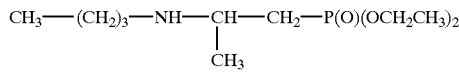

Step 1

A mixture of 29 g (0.314 mol; 1 eq.) of chloroacetone and 52 g of triethyl phosphite (0.314 mol; 1 eq.) is refluxed for 4 hours at 160° C.

6 g of diethylacetylmethane phosphonate are obtained after distillation under vacuum (1 mmHg; t=98° C.) (yield: 10%).

Step 2

A mixture of 1 g of the β-acetophosphonate obtained in step 1 (5.15×10$^{-3}$ mol/l eq.) is stirred for 8 hours under an inert atmosphere, at room temperature, with 0.40 g of n-butylamine (1 eq.), 1.64 g of NaBH(OAc)$_3$ (7.73×10$^{-3}$ mol, i.e. 1.5 eq.) and 0.33 g of acetic acid (5.7×10$^{-3}$ mol/1.1 eq.) in 10 ml of dichloroethane.

Step 3

5 ml of water are added to the reaction mixture. The solution is acidified with 35% HCl solution. The impurities are extracted with 3×10 ml of dichloromethane. The aqueous phase is then basified with NaOH solution. The expected compound is then extracted with 3×10 ml of dichloromethane. The organic phases are dried over MgSO$_4$ and then evaporated. 0.7 g of the title compound is obtained (55% yield).

Example 11

Synthesis of 2,5-bis(Diethoxyphosphoryl) pyrrolidine

Acetyl chloride (7.8 g; 0.1 mol) is added dropwise over 10 minutes to a mixture of freshly distilled butanedial (0.05 mol), acetamide (14.7 g; 0.25 mol) and acetic acid (50 ml) maintained at 0° C. with vigorous stirring.

The solution is then stirred for 12 hours at room temperature. The mixture is then cooled to 0° C. and phosphorus trichloride PCl$_3$ (8.8 g; 0.1 mol) is introduced dropwise with vigorous stirring over 15 minutes. The reaction mixture is then refluxed on a water bath for 1 hour, after which it is evaporated under reduced pressure. The oily residue is taken up in 100 ml of 12 M hydrochloric acid and refluxed for 12 hours, then evaporated under reduced pressure on a water bath. The residue is treated with 60 ml of methanol and the ammonium chloride precipitate thus obtained is filtered off and then washed with two successive fractions of 20 ml of methanol. The methanol fractions are combined and then evaporated under reduced pressure, after which the residue obtained is dissolved in a minimum amount of water. The aqueous solution is passed through an ion exchange column (Dowex 50*2-100, H$^+$ form) and eluted with water. The pyrrolidine-2,5-diphosphonic acid is obtained in a yield of 39%. Reference: I. van Assche et al., 51991) Eur. J. Med. Chem. 26, 505–515.

This diphosphonic acid can be esterified using a trialkyl orthoformate HC(OR)$_3$ in the presence of para-toluenesulphonic acid (R=CH$_3$ or C$_2$H$_5$). For general esterification methods, a person skilled in the art will refer to the reference article: U.S. Schollkopf et al., (1985) Liebigs Ann. Chem. 555–559.

Example 12

Synthesis of Ethyl 2-Methylpyrrolidin-2-ylmethylphosphinate of Formula

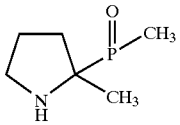

0.8 g (7.4 mmol) of ethyl methylphosphinate of formula (CH$_3$)(H)P(O)OC$_2$H$_5$ and 488 mg (8 mmol) of triethylamine are dissolved in 20 ml of anhydrous methylene chloride and cooled to 0° C. 0.87 g (8 mmol) of trimethylsilyl chloride is then added. The formation of the intermediate P(OSiMe$_3$)(OEt)(Me) is virtually instantaneous. 0.63 g (7.6 mmol) of 2-methylpyrroline of formula:

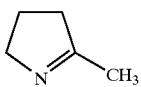

is added slowly. The mixture is then left stirring at room temperature. After 20 hours, the reaction monitoring by $^{31}$P NMR shows no further appreciable progress. The mixture is then hydrolysed with 20 ml of aqueous 10% hydrochloric acid solution and then purified by acid-base treatment. After extraction with methylene chloride, drying over anhydrous Na$_2$SO$_4$ and evaporation under vacuum, 1.1 g of crude product are obtained. Purification on a preparative plate gives 760 mg of the pure expected compound. Yield: 53%.

NMR:

Diestereoisomer 1:

$^1$H (400 MHz; CDCl$_3$); δ (ppm) 4.07 (m, O—C$\underline{H}_2$—CH$_3$); 2.8 to 3.1 (m, C$\underline{H}_2$—N); 1.5 to 2.2 (m, C$\underline{H}_2$—C$\underline{H}_2$—CH$_2$—N); 1.43 (d; J=12.9 Hz; C$\underline{H}_3$—C$_{quat.}$); 1.29 (d; J=14.75 Hz; C$\underline{H}_3$—P); 1.28 (t; J=7 Hz; O—CH$_2$—C$\underline{H}_3$). $^{13}$C (100.61 MHz; CDCl$_3$); δ (ppm) 60.68 (d; J=7.2 Hz; O—$\underline{C}$H$_2$—CH$_3$); 60.61 (d; J=118 Hz; $\underline{C}_{quat.}$); 47.3 (d; J=8 Hz; $\underline{C}$H$_2$—C$_{quat.}$); 34.06 (d; J=4 Hz; $\underline{C}$H$_2$—CH$_2$ —C$_{quat.}$): 26.08 ($\underline{C}$H$_2$—N); 23.13 (d; J=8.2 Hz; $\underline{C}$H$_3$—C$_{quat.}$); 16.77 (O—CH$_2$—$\underline{C}$H$_3$); 9.62 (d; J=87.5 Hz; $\underline{C}$H$_3$—P). $^{31}$P (40.53 MHz; CDCl$_3$): δ (ppm) 57.52.

Diestereoisomer 2:

$^1$H (400 MHz; CDCl$_3$); δ (ppm) 4.07 (m, O—CH$_2$—CH$_3$); 2.8 to 3.1 (m, C$\underline{H}_2$—N); 1.5 to 2.2 (m, C$\underline{H}_2$—C $\underline{H}_2$—CH$_2$—N); 1.42 (d; J=12.8 Hz; C$\underline{H}_3$—C$_{quat}$); 1.27 (t; J=7 Hz; O—CH$_2$—C$\underline{H}_3$); 1.26 (d; J=1.26 Hz; C$\underline{H}_3$—P). $^{13}$C (100.61 MHz; CDCl$_3$); δ (ppm) 60.62 (d; J=7.1 Hz; O—$\underline{C}H_2$—CH$_3$); 60.53 (d; J=118.8 Hz; $\underline{C}$quat.); 47.25 (d; J=7.9 Hz; $\underline{C}H_2$—C$_{quat}$); 33.52 (d; J=4.2 Hz; $\underline{C}H_2$—CH$_2$—C$_{quat}$); 26.04 ($\underline{C}H_2$—N); 23.31 (d; J=7.7 Hz; $\underline{C}H_3$—C$_{quat}$); 16.69 (O—CH$_2$—$\underline{C}H_3$); 9.44 (d; J=87 Hz; $\underline{C}H_3$—P) $^{31}$P (40.53 MHz; CDCl$_3$): δ (ppm) 57.30.

What is claimed is:

1. A pH marker of formula:

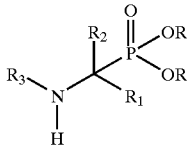

(I.1)

in which:
R is selected from the group consisting of (C$_1$–C$_{18}$)alkyl and (C$_6$–C$_{10}$)aryl;

R$_1$ and R$_2$ are independently selected from the group consisting of a deuterium atom; a halogen atom; a (C$_1$–C$_{18}$)alkyl group unsubstituted or substituted with one or more radicals selected from the group consisting of (C$_1$–C$_6$)alkoxy, (C$_3$–C$_{11}$)cycloalkyl, halogen, (C$_6$–C$_{10}$)aryl and nitro; a (C$_6$–C$_{10}$)aryl group unsubstituted or substituted with one or more radicals selected from the group consisting of (C$_1$–C$_6$)alkyl, (C$_1$–C$_6$)alkoxy, halogen, nitro and (C$_3$–C$_{11}$)cycloalkyl; (C$_1$–C$_{18}$)alkoxy substituted with one or more radicals selected from the group consisting of (C$_1$–C$_6$)alkoxy, halogen, nitro, (C$_3$–C$_{11}$)cycloalkyl and (C$_6$–C$_{10}$)aryl; a nitro group; and a (C$_3$–C$_{11}$)cycloalkyl group unsubstituted or substituted with one or more radicals selected from the group consisting of (C$_1$–C$_6$)alkyl, (C$_1$–C$_6$)alkoxy, halogen and nitro;

R$_3$ is selected from the group consisting of a deuterium atom; a linear (C$_5$–C$_{18}$)alkyl group unsubstituted or substituted with one or more radicals selected from the group consisting of nitro, halogen, (C$_1$–C$_6$)alkoxy and (C$_3$–C$_{11}$)cycloalkyl; and a (C$_3$–C$_{11}$)cycloalkyl group unsubstituted or substituted with one or more radicals selected from the group consisting of (C$_1$–C$_6$)alkyl, (C$_1$–C$_6$)alkoxy, halogen and nitro;

it being understood that:
when R represents ethyl and R$_1$ and R$_2$ represent propyl, then R$_3$ does not represent dodecyl; and
when R represents iso-C$_8$H$_{17}$ and R$_1$ and R$_2$ represent methyl, then R$_3$ does not represent hexyl;
or the salts thereof with a pharmaceutically acceptable acid.

2. Compound according to claim 1, of formula (I.1) in which R$_3$ represents a linear (C$_5$–C$_6$)alkyl group, unsubstituted or substituted with one or more radicals selected from the group consisting of nitro, halogen, (C$_1$–C$_6$)alkoxy and (C$_3$–C$_8$)cycloalkyl.

3. Compound according to claim 1, of formula (I.1) in which R$_1$ and R$_2$ are independently selected from the group consisting of a (C$_1$–C$_6$)alkyl group unsubstituted or substituted with one or more radicals selected from the group consisting of (C$_1$–C$_6$)alkoxy, (C$_5$–C$_6$)cycloalkyl, halogen, (C$_6$–C$_{10}$)aryl and nitro; and a (C$_6$–C$_{10}$)aryl group unsubstituted or substituted with one or more radicals selected from the group consisting of (C$_1$–C$_6$)alkyl, (C$_1$–C$_6$)alkoxy, halogen, nitro and (C$_5$–C$_6$)cycloalkyl; and R is selected from the group consisting of a (C$_1$–C$_6$)alkyl group and a (C$_6$–C$_{10}$)aryl group.

4. Compound according to claim 1, of formula (I.1) in which R$_3$ represents a linear (C$_5$–C$_6$)alkyl group; and R$_1$ and R$_2$ are independently selected from the group consisting of (C$_1$–C$_6$)alkyl and phenyl unsubstituted or substituted with one or more radicals selected from the group consisting of (C$_1$–C$_6$)alkyl, (C$_1$–C$_6$)alkoxy, halogen, nitro and (C$_5$–C$_6$)cycloalkyl.

5. A pH marker of formula:

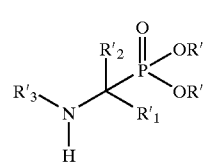

(I.2)

in which:
R' is selected from the group consisting of a hydrogen atom; a (C$_1$–C$_{18}$)alkyl and a (C$_6$–C$_{10}$)aryl group;

R'$_1$ is selected from the group consisting of a hydrogen atom; a deuterium atom; a halogen atom; a (C$_1$–C$_{18}$) alkyl group optionally substituted with one or more radicals selected from the group consisting of (C$_1$–C$_6$) alkoxy, (C$_3$–C$_{11}$)cycloalkyl, halogen, (C$_6$–C$_{10}$)aryl and nitro; a (C$_6$–C$_{10}$)aryl group unsubstituted or substituted with one or more radicals selected from the group consisting of (C$_1$–C$_6$)alkyl, (C$_1$–C$_6$)alkoxy, halogen, nitro and (C$_3$–C$_{11}$)cycloalkyl; (C$_1$–C$_{18}$)alkoxy unsubstituted or substituted with one or more radicals selected from the group consisting of (C$_1$–C$_6$)alkoxy, halogen, nitro, (C$_3$–C$_{11}$)cycloalkyl and (C$_6$–C$_{10}$)aryl; a nitro group; or a (C$_3$–C$_{11}$)cycloalkyl group unsubstituted or substituted with one or more radicals selected from the group consisting of (C$_1$–C$_6$)alkyl, (C$_1$–C$_6$) alkoxy, halogen and nitro;

R'$_2$ and R'$^3$ together form a divalent radical:

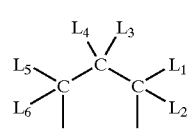

(a)

in which the group —C(L$_1$)(L$_2$)— is directly linked to the carbon bearing R'$_1$,
and in which L$_1$, L$_2$, L$_3$ and L$_4$ are, independently of each other selected from the group consisting of a hydrogen atom, a deuterium atom, a (C$_1$–C$_{18}$)alkyl and a (C$_6$–C$_{10}$)aryl group;

L$_5$ and L$_6$ being defined as follows:
when R'$_1$ is selected from the group consisting of a hydrogen, halogen or deuterium atom, an unsubstituted or substituted (C$_1$–C$_{18}$)alkoxy group, a nitro group and an unsubstituted or substituted (C$_3$–C$_{11}$)cycloalkyl group, L$_5$ and L$_6$ are, independently of each other, selected from the group consisting of a hydrogen atom, a deuterium atom, a (C$_1$–C$_{18}$)alkyl group, a (C$_6$–C$_{10}$)aryl group and a group —P(O)(OR')$_2$;
when R'$_1$ is selected from the group consisting of an unsubstituted or substituted (C$_1$–C$_{18}$)alkyl and an unsubstituted or substituted (C$_6$–C$_{10}$)aryl, either L$_5$ or L$_6$ represents a hydrogen atom, and the other is selected from the group consisting of (C$_2$–C$_{18}$) alkyl and (C$_6$–C$_{10}$)aryl;

it being understood that when $L_1$, $L_2$, $L_3$, $L_4$, and either $L_5$ or $L_6$ represent a hydrogen atom, then:

if R' and $R'_1$ represent H, then $L_6$ is other than H;

if R' represents $(C_1-C_3)$alkyl and $R'_1$ represents methyl, then $L_6$ is neither ethyl nor isopropyl;

if R' represents $(C_1-C_3)$alkyl and $R'_1$ represents H, then $L_6$ is not hexyl;

or the salts thereof with a pharmaceutically acceptable acid, wherein if R' represents $(C_1-C_3)$alkyl and $R'_1$ represents H, then $L_6$ is neither hexyl nor methyl.

6. Compound according to claim 5, of formula (I.2) in which R' is selected from the group consisting of $(C_1-C_{18})$alkyl and $(C_6-C_{10})$aryl.

7. Compound according to claim 5, of formula (I.2) in which $R'_1$ is selected from the group consisting of $(C_1-C_6)$alkyl and a hydrogen atom and $R'_2$ and $R'_3$ together form a radical of formula:

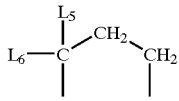

either $L_5$ or $L_6$ represents a hydrogen atom and the other represents $(C_2-C_{18})$alkyl or $(C_6-C_{10})$aryl, it being understood that when $R'_1$ represents methyl, then either $L_5$ or $L_6$ represents H and the other is other than ethyl or isopropyl.

8. Compound according to claim 5, of formula (I.2) in which $R'_1$ represents $(C_1-C_6)$alkyl, $R'_2$ and $R'_3$ together form a divalent radical:

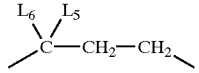

in which $L_5$ represents H and $L_6$ represents phenyl; and R' is selected from the group consisting of a $(C_1-C_6)$alkyl group, a $(C_6-C_{10})$aryl group and a hydrogen atom.

9. Compound according to claim 5, of formula (I.2) in which $R'_1$ represents a hydrogen atom and $R'_2$ and $R'_3$ together form a divalent radical:

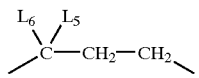

in which $L_5$ represents H and $L_6$ represents $—P(C)(OR')_2$; and R' is selected from the group consisting of a $(C_1-C_6)$ alkyl group, a $(C_6-C_{10})$aryl group and a hydrogen atom.

10. Method of pH measurement by NMR spectroscopy comprising:

measuring pH with a pH-marker in $^{31}$P NMR, wherein said pH marker is a compound of formula:

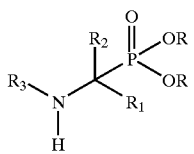

(I.1)

in which:

$T_1$ and $T_2$ independently represent a group —R or —OR;

R is selected from the group consisting of a $(C_1-C_{18})$ alkyl and $(C_6-C_{10})$aryl group;

$R_1$ and $R_2$ are independently selected from the group consisting of a hydrogen atom; a deuterium atom; a halogen atom; a $(C_1-C_{18})$alkyl group unsubstituted or substituted with one or more radicals selected from the group consisting of $(C_1-C_6)$alkoxy, $(C_3-C_{11})$cycloalkyl, halogen, $(C_6-C_{10})$ aryl and nitro; a $(C_6-C_{10})$aryl group unsubstituted or substituted with one or more radicals selected from the group consisting of $(C_1-C_6)$alkyl, $(C_1-C_6)$alkoxy, halogen, nitro and $(C_3-C_{11})$ cycloalkyl, $(C_1-C_{18})$ alkoxy unsubstituted or substituted with one or more radicals selected from the group consisting of $(C_1-C_6)$alkoxy, halogen, nitro, $(C_3-C_{11})$cycloalkyl and $(C_6-C_{10})$aryl; a nitro group; a group $—P(O)(OR)_2$, and a $(C_3-C_{11})$cycloalkyl group or substituted with one or more radicals selected from the group consisting of $(C_1-C_6)$alkyl, $(C_1-C_6)$alkoxy, halogen and nitro;

$R_3$ is selected from the group consisting of a hydrogen and a deuterium atom; a $(C_1-C_{19})$alkyl group unsubstituted or substituted with one or more radicals selected from the group consisting of nitro, halogen, $(C_1-C_6)$alkoxy, $(C_6-C_{10})$aryl and $(C_3-C_{11})$cycloalkyl, and optionally bearing a group $—P(O)(OR)_2$ in position 1; a $(C_3-C_{11})$ cycloalkyl, group unsubstituted or substituted with one or more radicals selected from the group consisting of $(C_1-C_6)$alkyl, $(C_6-C_{10})$alkoxy, nitro, halogen and $(C_3-C_{11})$cycloalkyl;

p represents 0 or 1;

A represents a divalent radical $—CR_4R_5—$ in which $R_4$ and $R_5$ have the meanings given above for $R_1$ and $R_2$ with the exclusion of $—P(O)(OR)_2$; it being understood that the said compound does not contain more than two groups $—P(O)(OR)_2$;

or a salt thereof with pharmaceutically acceptable acid.

11. Method according to claim 10, wherein said pH-marker is a compound of formula (II.1) in which $R_3$ is other than a hydrogen atom.

12. Method according to claim 10, wherein said pH-marker is a compound of formula (II.1) in which $R_1$ and $R_2$ are both other than a hydrogen atom.

13. Method according to claim 11, wherein said pH-marker is a compound of formula (II.1) in which p represents 0.

14. Method according to claim 13, wherein said pH-marker is a compound of formula (II.1) in which $R_3$ is selected from the group consisting of a $(C_1-C_6)$alkyl group unsubstituted or substituted with one or more radicals selected from the group consisting of nitro, halogen, $(C_1-C_6)$alkoxy, $(C_6-C_{10})$aryl and $(C_3-C_8)$cycloalkyl, and optionally bearing a group $—P(O)(OR)_2$ in position 1.

15. Method according to claim 13, wherein said pH-marker is a compound of formula (II.1) in which $R_1$ and $R_2$ are independently selected from the group consisting of a $(C_1-C_6)$alkyl group unsubstituted or substituted with one or more radicals selected from the group consisting of $(C_1-C_6)$alkoxy, $(C_5-C_6)$cycloalkyl, halogen, $(C_6-C_{10})$aryl and nitro; a $(C_6-C_{10})$aryl group unsubstituted or substituted with one or more radicals selected from the group consisting of $(C_1-C_6)$alkyl, $(C_1-C_6)$alkoxy, halogen, nitro and $(C_5-C_6)$ cycloalkyl; and a group $—P(O)(OR)_2$; and R is selected from the group consisting of a $(C_1-C_6)$alkyl group and a $(C_6-C_{10})$aryl group.

16. Method according to claim 13, wherein said pH-marker is a compound of formula (II.1) in which $R_3$ represents a $(C_1-C_6)$alkyl group; and $R_1$ and $R_2$ are independently selected from the group consisting of $(C_1-C_6)$ alkyl and phenyl unsubstituted or substituted with one or more radicals selected from the group consisting of $(C_1-C_6)$ alkyl, $(C_1-C_6)$alkoxy, halogen, nitro and $(C_5-C_6)$cycloalkyl and a group —P(O)(OR)$_2$.

17. Method according to claim 16, wherein said pH-marker is a compound selected from the group consisting of 2-propylamino-2-diethoxyphosphorylpropane, N-[1-phenyl-1-diethoxy-phosphorylethyl]-N-propylamine and N-[1,1-bis(diethoxyphosphoryl)methyl]-N-tert-butylamine.

18. Method according to claim 10, wherein said pH-marker is compound of formula (II.1) in which p represents 1; $R_3$ represents $(C_1-C_6)$alkyl; A represents —CR$_4$R$_5$—; $R_1$, $R_2$, $R_4$ and $R_5$ are independently selected from the group consisting of a hydrogen atom and a $(C_1-C_6)$ alkyl group; and R is selected from the group consisting of a $(C_1-C_6)$alkyl group and a $(C_6-C_{10})$aryl group.

19. Method according to claim 18, wherein said pH-marker is N-[(1-methyl-2-diethoxyphosphoryl)ethyl]-N-n-butylamine.

20. Method of pH measurement by NMR spectroscopy, comprises:
measuring pH-marker in $^{31}$P NMR, wherein said pH-marker is compound of formula

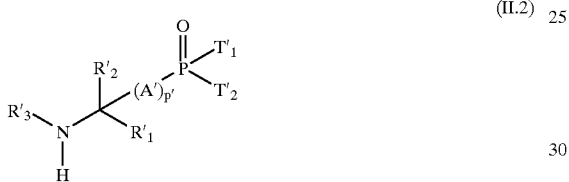

(II.2)

in which
T'$_1$ and T'$_2$ are independently a $(C_1-C_{18})$alkyl, $(C_6-C_{10})$aryl and —OR' group;
R' is selected from the group consisting of a hydrogen atom, $(C_1-C_{18})$alkyl and $(C_6-C_{10})$aryl;
R'$_1$ is selected from the group consisting of a hydrogen atom; a deuterium atom; a halogen atom; a $(C_1-C_{18})$ alkyl group unsubstituted or substituted with one or more radicals selected from the group consisting of $(C_1-C_6)$alkoxy, $(C_3-C_{11})$cycloalkyl, halogen $(C_6-C_{10})$aryl and nitro; a $(C_6-C_{18})$aryl group unsubstituted or substituted with one or more radicals selected from the group consisting of $(C_1-C_6)$alkyl, $(C_1-C_6)$alkoxy, halogen, nitro and $(C_3-C_{11})$ cycloalkyl; $(C_1-C_{18})$alkoxy unsubstituted or substituted with one or more radicals selected from the group consisting of $(C_1-C_6)$alkoxy, halogen, nitro, $(C_3-C_{11})$cycloalkyl and $(C_6-C_{10})$aryl; a nitro group; a group —P(O)(OR')$_2$; and a $(C_3-C_{11})$cycloalkyl group unsubstituted or substituted with one or more radicals selected from the group consisting of $(C_1-C_6)$alkyl, $(C_1-C_6)$alkoxy, halogen and nitro;
R'$_2$ and R'$_3$ together form a divalent radical;

(a)

in which the group —C(L$_1$)(L$_2$)— is directly linked to the carbon bearing R'$_1$ and in which
L$_1$, L$_2$, L$_3$ and L$_4$ are, independently of each other, selected from the group consisting of a hydrogen atom; a deuterium atom; a $(C_1-C_{18})$alkyl group unsubstituted or substituted with one or more radicals selected from the group consisting of $(C_1-C_6)$alkoxy, $(C_3-C_{11})$cycloalkyl, halogen, $(C_6-C_{10})$aryl and nitro; a $(C_6-C_{10})$aryl group unsubstituted or substituted with one or more radicals selected from the group consisting of $(C_1-C_6)$alkyl, $(C_1-C_6)$alkoxy, halogen, nitro and $(C_3-C_{11})$cycloalkyl; $(C_1-C_{18})$alkoxy unsubstituted or substituted with one or more radicals selected from the group consisting of $(C_1-C_6)$ alkoxy, halogen, nitro, $(C[3]_3-C[11]_{11})$ cycloalkyl and $(C_6-C_{10})$aryl; a nitro group; a group —P(O)(OR')$_2$; or a group $(C_3-C_{11})$ cycloalkyl unsubstituted or substituted with one or more radicals selected from the group consisting of $(C_1-C_6)$alkyl, $(C_1-C_6)$alkoxy, halogen and nitro; and L$_5$ and L$_6$ represent, independently of each others a hydrogen atom; a deuterium atom; a $(C_1-C_{18})$alkyl group unsubstituted or substituted with one or more radicals selected from the group consisting of $(C_1-C_6)$alkoxy, $(C_3-C_{11})$cycloalkyl, halogen, $(C_6-C_{10})$aryl and nitro; a $(C_6-C_{10})$aryl group unsubstituted or substituted with one or more radicals selected from the group consisting of $(C_1-C_6)$alkyl, $(C_1-C_6)$alkoxy, halogen, nitro and $(C_3-C_{11})$cycloalkyl; $(C_1-C_{18})$alkoxy unsubstituted or substituted with one or more radicals selected from the group consisting of $(C_1-C_6)$ alkoxy, halogen, nitro, $(C_3-C_{11})$cycloalkyl and $(C_6-C_{10})$aryl; a nitro group; a group —P(O)(OR')$_2$; and a $(C_3-C_{11})$cycloalkyl group unsubstituted or substituted with one or more radicals selected from the group consisting of $(C_1-C_6)$ alkyl, $(C_1-C_6)$alkoxy, halogen and nitro; and a group —P(O)(OR')$_2$;
p' represents 0 or 1;
A' represents a divalent radical —CR'$_4$R'$_5$— in which R'$_4$ and R'$_5$ have the meanings given above for R'$_1$ with the exclusion of —P(O)(OR')$_2$;
it being understood that the said compound does not contain more that two groups —P(O)(OR')$_2$;
or a salt thereof with a pharmaceutically acceptable acid.

21. Method according to claim 20, in which R' is other than a hydrogen atom.

22. Method according to claim 20, wherein said pH-marker is a compound formula (II.2) in which R'$_1$ is selected from the group consisting of a hydrogen atom, a $(C_1-C_6)$ alkyl group, a $(C_6-C_{10})$aryl group and a —P(O)(OR')$_2$ and R'$_2$ and R'$_3$ together form a radical of formula:

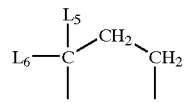

in which L$_5$ and L$_6$ are as defined in claim 20.

23. Method according to claim 21, wherein said pH-marker is a compound of formula (II.2) in which L$_5$ and L$_6$ are independently selected from the group consisting of from a hydrogen atom, a $(C_1-C_6)$alkyl group, a $(C_6-C_{10})$aryl group and a group —P(O)(OR')$_2$, R' being selected from the group consisting of a $(C_1-C_6)$alkyl group, a $(C_6-C_{10})$aryl group and a hydrogen atom.

24. Method according to claim 21, wherein said pH-marker is a compound selected from the group consisting of:

2-methyl-2-diethoxyphosphorylpyrrolidine;
2,2-bis(diethoxyphosphoryl)pyrrolidine;
2,2-bis(diisopropoxyphosphoryl)pyrrolidine;
2,5-bis(diethoxyphosphoryl)-2,5-dimethyl-pyrrolidine;
trans-2,5-bis(diethoxyphosphoryl)pyrrolidine;
ethyl 2-methylpyrrolidin-2-ylmethylphosphinate;
2-phenyl-2-diethoxyphosphorylpyrrolidine; and
2-methyl-2-diethoxyphosphoryl-5-phenylpyrrolidine.

25. Method according to claim 10, wherein $T_1$ represents —OR and $T_2$ represents —R.

26. Method according to claim 11, wherein $T_1$ and $T_2$ represent —OR.

27. Method according to claim 20, wherein $T'_1$ represents —OR' and $T'_2$ is selected from the group consisting of $(C_1–C_{18})$alkyl and $(C_6–C_{10})$aryl.

28. Method according to claim 20, wherein $T'_1$ and $T'_2$ represent —OR'.

* * * * *